(12) United States Patent
Clark

(10) Patent No.: US 11,001,872 B2
(45) Date of Patent: May 11, 2021

(54) DESIGNING CUSTOMIZED PROTEIN-SPECIFIC BUFFER SYSTEM

(71) Applicant: Shawn Clark, Marlborough, MA (US)

(72) Inventor: Shawn Clark, Marlborough, MA (US)

( * ) Notice: Subject to any disclaimer, the term of this patent is extended or adjusted under 35 U.S.C. 154(b) by 373 days.

(21) Appl. No.: 15/761,936

(22) PCT Filed: Sep. 22, 2016

(86) PCT No.: PCT/US2016/053109
§ 371 (c)(1),
(2) Date: Mar. 21, 2018

(87) PCT Pub. No.: WO2017/053567
PCT Pub. Date: Mar. 30, 2017

(65) Prior Publication Data
US 2018/0282782 A1    Oct. 4, 2018

Related U.S. Application Data

(60) Provisional application No. 62/221,802, filed on Sep. 22, 2015.

(51) Int. Cl.
| | | |
|---|---|---|
| *G01N 33/68* | (2006.01) | |
| *C12Q 1/34* | (2006.01) | |
| *B01L 3/00* | (2006.01) | |
| *C12Q 1/533* | (2006.01) | |

(52) U.S. Cl.
CPC ............ *C12Q 1/34* (2013.01); *B01L 3/50851* (2013.01); *C12Q 1/533* (2013.01); *C12Y 306/05005* (2013.01); *C12Y 502/01014* (2015.07); *G01N 33/6803* (2013.01); *B01L 2200/16* (2013.01)

(58) Field of Classification Search
CPC ... B01L 3/50851; B01L 2200/16; C12Q 1/25; G01N 33/573; G01N 33/6803
See application file for complete search history.

(56) References Cited

U.S. PATENT DOCUMENTS

| | | | |
|---|---|---|---|
| 3,817,837 A | 6/1974 | Rubenstein et al. | ............ 435/7.9 |
| 3,850,752 A | 11/1974 | Schuurs et al. | ............ 435/7.93 |
| 3,939,350 A | 2/1976 | Kronick et al. | ............ 250/365 |
| 3,996,345 A | 12/1976 | Ullman et al. | ............ 436/537 |
| 4,275,149 A | 6/1981 | Litman et al. | ............ 435/7.91 |
| 4,277,437 A | 7/1981 | Maggio | ............ 422/401 |
| 4,366,241 A | 12/1982 | Tom et al. | ............ 435/7.91 |

(Continued)

OTHER PUBLICATIONS

Koshland, D. E. (1958) "Application of a Theory of Enzyme Specificity to Protein Synthesis," *Proceedings of the National Academy of Sciences* 44(2), 98.

(Continued)

*Primary Examiner* — Jill A Warden
*Assistant Examiner* — Dwayne K Handy
(74) *Attorney, Agent, or Firm* — Medlen & Carroll, LLP

(57) ABSTRACT

The present invention is related to the field of protein chemistry. In particular, mixed buffer compositions are formulated that allow an accurate identification of agent-induced changes in protein melting point temperatures. Such buffer compositions provide for methods that determine the specific effects of exogenous agents on protein stability, cryoprotective effects and/or protein quality control (e.g., synthesis and/or extraction purity validations).

15 Claims, 24 Drawing Sheets

(56) References Cited

U.S. PATENT DOCUMENTS

| | | | |
|---|---|---|---|
| 7,749,712 B2* | 7/2010 | Pulli | G01N 33/542 435/7.1 |
| 7,985,733 B1 | 7/2011 | Motheram | 514/13 |
| 8,183,046 B2* | 5/2012 | Lu | A01N 1/02 436/18 |
| 8,609,423 B2 | 12/2013 | Diller et al. | 436/86 |
| 9,012,173 B2 | 4/2015 | Franciskovich et al. | 435/31 |
| 2001/0003648 A1* | 6/2001 | Pantoliano | C40B 30/04 435/4 |
| 2004/0219074 A1* | 11/2004 | Childers | B01L 3/5085 422/534 |
| 2007/0202010 A1* | 8/2007 | Talebpour | B01L 3/50853 422/400 |
| 2008/0171393 A1 | 7/2008 | Lu et al. | 436/18 |
| 2014/0094593 A1 | 4/2014 | Frauenschuh | 530/387.3 |
| 2014/0315190 A1* | 10/2014 | Bornarth | C09B 23/145 435/6.1 |

OTHER PUBLICATIONS

Blatny, P. et al. (1997) "Trace determination of iron in water at the μg/l level by on-line coupling of capillary isotachophoresis and capillary zone electrophoresis with UV detection of the EDTA-FE(III) complex," *Journal of Chromatography A*757(1), 297-302.

Castells, C. B. et al. (2003) "Effect of temperature on pH measurements and acid—base equilibria in methanol—water mixtures," *Journal of Chromatography A*1002(1), 41-53.

Ciulli, A. et al. (2007) "Fragment-based approaches to enzyme inhibition," *Current Opinion in Biotechnology*18(6), 489-496.

Ericsson, U. B. et al. (2006) "Thennofluor-based high-throughput stability optimization of proteins for structural studies," *Analytical Biochemistry*357(2), 289-298.

Fabrice, G. (2009) "The Morpheus protein crystallization screen," *Journal of Applied Crystallography*42(6), 1035-1042.

Haahr, L. T. (2012) Purification and Characterization of Tryptophan Hydroxylase, in *Metalloprotein Chemistry & Engineering, DTU Chemistry*, Technical University of Denmark.

Higgins, J. A. et al. (2003) "A handheld real time thermal cycler for bacterial pathogen detection," *Biosensors and Bioelectronics*18(9), 1115-1123.

Kipp, J. E. et al. (1995) "Computer Simulation of the Effect of Temperature on pH," *Journal of Pharmaceutical Sciences*84(11), 1347-1352.

Kranz, J. K. et al. (2011) "Chapter eleven—Protein Thermal Shifts to Identify Low Molecular Weight Fragments," in *Methods in Enzymology*(Kuo, L. C., Ed.), pp. 277-298, Academic Press.

Linderstrom-Lang, K. U. et al. (1959) "Protein structure and enzyme activity," *The Enzymes*1(2), 443-510.

Lo, M.-C. et al. (2004) "Evaluation of fluorescence-based thermal shift assays for hit identification in drug discovery," *Analytical Biochemistry*332(1), 153-159.

Luft, J. R. et al. (2010) "Crystal Cookery—Using High-Throughput Technologies and the Grocery Store As a Teaching Tool," *Journal of Applied Crystallography*43, 1189-1207.

Niesen, F. H. et al. (2007) "The use of differential scanning fluorimetry to detect ligand interactions that promote protein stability," *Nature Protocols*2, 2212.

Pantoliano, M. W. et al. (2001) "High-density miniaturized thermal shift assays as a general strategy for drug discovery," *Journal of Biomolecular Screening*6(6), 429-440.

Reinhard, L. et al. (2013) "Optimization of protein buffer cocktails using Thermofluor," *Acta Crystallographica Section F: Structural Biology and Crystallization Communications*69(Pt 2), 209-214.

Taha, M. et al. (2014) "Good's buffers as a basis for developing self-buffering and biocompatible ionic liquids for biological research," *Green chemistry: an international journal and green chemistry resource*: GC 16(6), 3149-3159.

Vespalec, R. et al. (2004) "Aggregation and other intermolecular interactions of biological buffers observed by capillary electrophoresis and UV photometry," *Journal of Chromatography A*1051(1), 75-84.

Weier, H. U. et al. (1988) "A programmable system to perform the polymerase chain reaction," *DNA*7(6), 441-447.

PCT International Search Report of International Application No. PCT/US2016/053109 dated Feb. 6, 2017.

* cited by examiner

Figure 16A
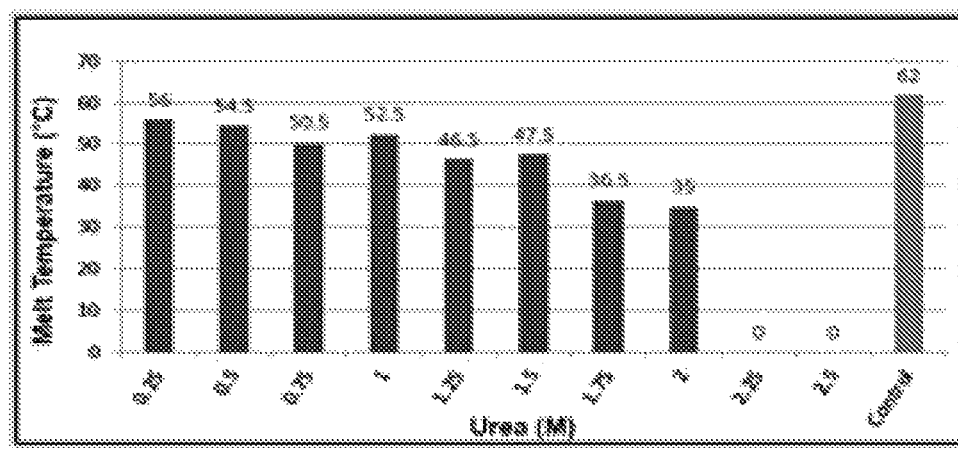
Figure 16B
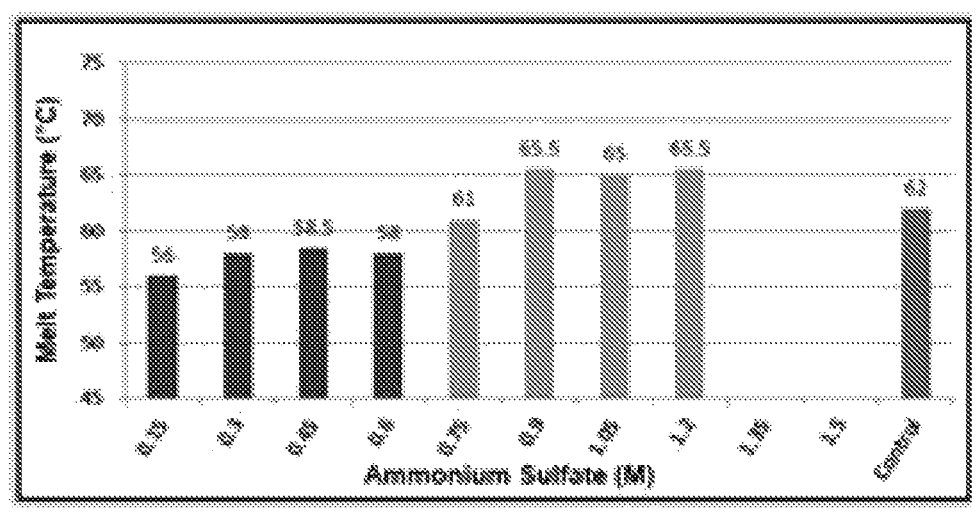
Figure 16

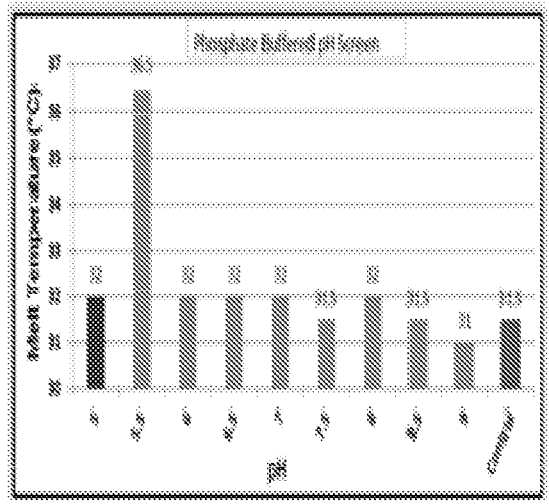 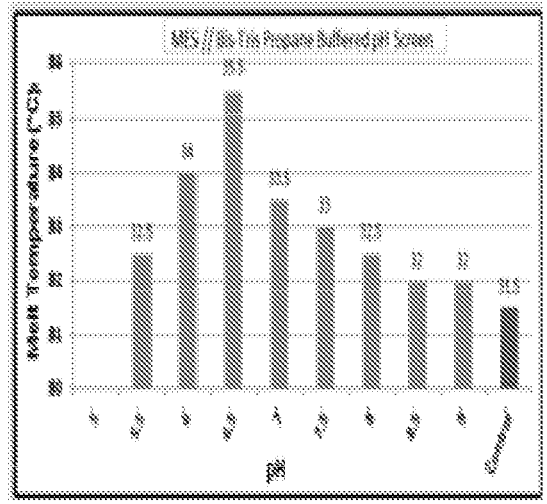
Figure 17A            Figure 17B
Figure 17

DESIGNING CUSTOMIZED PROTEIN-SPECIFIC BUFFER SYSTEM

FIELD OF THE INVENTION

The present invention is related to the field of protein chemistry. In particular, mixed buffer compositions are formulated that allow an accurate identification of agent-induced changes in protein melting point temperatures. Such mixed buffer compositions provide for methods that determine the specific effects of exogenous agents on protein stability, cryoprotective effects and/or protein quality control (e.g., for synthesis and/or extraction purity validations). Optimal exogenous agents are then selected for inclusion into customized buffer systems that are protein-specific.

BACKGROUND

The feasibility of a process of describing a proteins' stability and/or performing a protein analysis using heat and a hydrophobic dye has been discussed for decades. Ericsson et al., (2006). "Thermofluor-based high-throughput stability optimization of proteins for structural studies." Analytical Biochemistry 357 (2): 289-298. However, until the present disclosure, those in the art had not solved all the problems known to exist to generate a stable platform that provides consistent and accurate data.

Protein analysis has conventionally been limited to temperature scans where buffer solutions were necessarily different at various temperatures due to the necessity to have buffers with compatible pKa's at each specific temperature. Furthermore, commercially available instrumentation to perform protein melting point temperature scans are limited to a few sources. For example, most of these available instruments are primarily designed to determine protein melting points using only buffer formulations provided with the instruments but are also capable of performing ligand binding studies.

What is lacking in the art are compositions and methods that can be used to derive customized buffer formulations for specific proteins. Using these customized buffer systems, one of skill in the art will be able to develop, purify and store commercial proteins under conditions that maximize stability, cryoprotection and accurately monitor protein quality control.

SUMMARY OF THE INVENTION

The present invention is related to the field of protein chemistry. In particular, mixed buffer compositions are formulated that allow an accurate identification of agent-induced changes in protein melting point temperatures. Such mixed buffer compositions provide for methods that determine the specific effects of exogenous agents on protein stability, cryoprotective effects and/or protein quality control (e.g., for synthesis and/or extraction purity validations). Optimal exogenous agents are then selected for inclusion into customized buffer systems that are protein-specific.

In one embodiment, the present invention contemplates a device, comprising:
a) a solid substrate comprising a plurality of testing wells and a control well, wherein each of said plurality of testing wells comprises a first buffer and a second buffer, said control well comprises a sample buffer, and each of said plurality of testing wells and control well comprises a protein sample;
b) a first testing well series of said plurality of testing wells, wherein each well of said first testing well series comprises a different ammonium sulphate concentration;
c) a second testing well series of said plurality of testing wells, wherein each well of said second testing well series comprises a different amino acid;
d) a third testing well series of said plurality of testing wells, wherein each well of said third testing well series comprises a different urea concentration;
e) a fourth testing well series of said plurality of testing wells, wherein each well of said fourth testing well series comprises a different glycerol concentration;
f) a fifth testing well series of said plurality of testing wells, wherein each well of said fifth testing well series comprises a different hydrogen ion concentration;
g) a sixth testing well series of said plurality of testing wells, wherein each well of said sixth testing well series comprises a different third buffer;
h) a seventh testing well series of said plurality of testing wells, wherein each well of said seventh testing well series comprises a different dimethyl sulfoxide concentration;
i) an eighth testing well series of said plurality of testing wells, wherein each well of said eighth testing well series comprises a different Hoefmeister Series compound; and
j) a ninth testing well series of said plurality of testing wells, wherein each well of said ninth testing well series comprises an different metal ion.

In one embodiment, the device is configured for compatibility with a thermocycler. In one embodiment, the thermocycler is a real time thermocycler. In one embodiment, the thermocycler is configured for compatibility with an optical reaction module. In one embodiment, the optical reaction module is a differential scanning fluorimeter. In one embodiment, the optical reaction module is configured with an optically readable storage medium device. In one embodiment, the first buffer includes, but is not limited to, MES, citrate and/or cacodylate. In one embodiment, the second buffer includes, but is not limited to, bis-tris propane, bicine and/or HEPES. In one embodiment, the first buffer is at a concentration of 100 mM. In one embodiment, the second buffer is at a concentration of 100 mM. In one embodiment, the different ammonium sulphate concentration ranges between approximately 0.15-1.5%. In one embodiment, the different ammonium sulphate concentration is 0.15%. In one embodiment, the different ammonium sulphate concentration is 0.3%. In one embodiment, the different ammonium sulphate concentration is 0.45%. In one embodiment, the different ammonium sulphate concentration is 0.6%. In one embodiment, the different ammonium sulphate concentration is 0.75%. In one embodiment, the different ammonium sulphate concentration is 0.9%. In one embodiment, the different ammonium sulphate concentration is 1.05%. In one embodiment, the different ammonium sulphate concentration is 1.2%. In one embodiment, the different ammonium sulphate concentration is 1.35%. In one embodiment, the different ammonium sulphate concentration is 1.5%. In one embodiment, the different urea concentration ranges between approximately 0.25-2.5%. In one embodiment, the different urea concentration is 0.25%. In one embodiment, the different urea concentration is 0.5%. In one embodiment, the different urea concentration is 0.75%. In one embodiment, the different urea concentration is 1.0%. In one embodiment, the different urea concentration is 1.25%. In one embodiment, the different urea concentration is 1.50%. In one embodiment, the different urea concentration is 1.75%. In one embodiment, the different urea concentration is 2.0%. In one embodiment, the different urea concentration is 2.25%. In one embodiment, the different urea concentration is 2.5%. In one embodiment, the different hydrogen ion concentration ranges between approximately pH 5.0-9.0. In one embodiment, the different hydrogen ion concentration is pH 5.0. In one embodiment, the different hydrogen ion concentration is pH 5.5. In one embodiment, the different hydrogen ion concentration is pH 6.0. In one embodiment, the different hydrogen ion concentration is pH 6.5. In one embodiment, the different hydrogen ion concentration is pH 7.0. In one embodiment, the different hydrogen ion concentration is pH 7.5. In one embodiment, the different hydrogen ion concentration is pH 8.0. In one embodiment, the different hydrogen ion concentration is pH 8.5. In one embodiment, the different hydrogen ion concentration is pH 9.0. In one embodiment, the different dimethyl sulfoxide concentration ranges between approximately 0.5-10%. In one embodiment, the different dimethyl sulfoxide concentration is 0.5%. In one embodiment, the different dimethyl sulfoxide concentration is 1%. In one embodiment, the different dimethyl sulfoxide concentration is 2%. In one embodiment, the different dimethyl sulfoxide concentration is 3%. In one embodiment, the different dimethyl sulfoxide concentration is 4%. In one embodiment, the different dimethyl sulfoxide concentration is 5%. In one embodiment, the different dimethyl sulfoxide concentration is 6%. In one embodiment, the different dimethyl sulfoxide concentration is 7%. In one embodiment, the different dimethyl sulfoxide concentration is 8%. In one embodiment, the different dimethyl sulfoxide concentration is 9%. In one embodiment, the different dimethyl sulfoxide concentration is 10%. In one embodiment, the different metal ion includes, but is not limited to, zinc chloride, copper chloride, manganese chloride, cobalt chloride and/or nickel chloride. In one embodiment, the different metal ion has a concentration of 5 μM. In one embodiment, the different metal ion has a concentration of 25 μM. In one embodiment, the different Hoefmeister Series compound includes, but is not limited to, sodium fluoride, sodium chloride, sodium iodide, sodium thiocyanate, sodium nitrate, sodium formate, sodium acetate trihydrate, sodium sulphate decahydrate, sodium tartrate dibasic, sodium phosphate dibasic, sodium citrate tribasic, ammonium chloride, potassium chloride, sodium chloride, lithium chloride, magnesium chloride hexahydrate, calcium chloride dihydrate and/or guanidine-HCl. In one embodiment, the different Hoefmeister Series compound is at a concentration of 50 mM. In one embodiment, the different third buffer includes, but is not limited to, Trizma, HEPES, Pipes, Bicine, Bis-Tris, TES, MOPS, MES, PBS, CAPS, CHES, Bis-Tris Propane and TAPS. In one embodiment, the different third buffer has a pH 7.0. In one embodiment, the different third buffer has a pH 9.0. In one embodiment, the different third buffer is at a concentration of 100 mM. In one embodiment, the different glycerol concentration ranges between approximately 2.5-25%. In one embodiment, the different glycerol concentration is 2.5%. In one embodiment, the different glycerol concentration is 5%. In one embodiment, the different glycerol concentration is 7.5%. In one embodiment, the different glycerol concentration is 10%. In one embodiment, the different glycerol concentration is 12.5%. In one embodiment, the different glycerol concentration is 15.0%. In one embodiment, the different glycerol concentration is 17.5%. In one embodiment, the different glycerol concentration is 20%. In one embodiment, the different glycerol concentration is 22.5%. In one embodiment, the different glycerol concentration is 25%. In one embodiment, the different amino acid includes, but is not limited to, arginine, glutamic acid, glycine and/or lysine. In one embodiment, the different amino acid is at a concentration of 25 mM.

In one embodiment, the present invention contemplates a device, comprising:
  a) a solid substrate comprising a plurality of testing wells and a control well, wherein each of said plurality of testing wells comprises a first buffer and a second buffer, said control well comprises a sample buffer, and each of said testing wells and control well comprises a protein sample;
  b) a first testing well series of said plurality of testing wells, wherein each well of said first testing well series comprises a different ethylene glycol concentration;
  c) a second testing well series of said plurality of testing wells, wherein each well of said second testing well series comprises a different polyethylene glycol 3350 MME concentration;
  d) a third testing well series of said plurality of testing wells, wherein each well of said third testing well series comprises a different erythritol concentration;
  e) a fourth testing well series of said plurality of testing wells, wherein each well of said fourth testing well series comprises a different 2-methyl-2,4 pentanediol concentration;
  f) a fifth testing well series of said plurality of testing wells, wherein each well of said fifth testing well series comprises a different polyethylene glycol 6000 concentration;
  g) a sixth testing well series of said plurality of testing wells, wherein each well of said sixth testing well series comprises a different sodium malonate concentration;
  h) a seventh testing well series of said plurality of testing wells, wherein each well of said seventh testing well series comprises a different ethanol concentration;
  i) an eighth testing well series of said plurality of testing wells, wherein each well of said eighth testing well series comprises a different polyethylene glycol 10,000 concentration;
  j) a ninth testing well series of said plurality of testing wells, wherein each well of said ninth testing well series comprises an different glycerol concentration;
  k) a tenth testing well series of said plurality of testing wells, wherein each well of said tenth testing well series comprises a different xylitol concentration;
  l) an eleventh testing well series of said plurality of testing wells, wherein each well of said eleventh testing well series comprises a different sucrose concentration;
  m) a twelfth testing well series of said plurality of testing wells, wherein each well of said twelfth testing well series comprises a different trehalose dihydrate concentration;
  n) a thirteenth testing well series of said plurality of testing wells, wherein each well of said thirteenth testing well series comprises a different 1,6 hexanediol concentration; and
  n) a fourteenth testing well series of said plurality of testing wells, wherein each well of said fourteenth testing well series comprises a different 1,2 propanediol concentration.

In one embodiment, the device is configured for compatibility with a thermocycler. In one embodiment, the thermocyler is a real time thermocycler. In one embodiment, the thermocycler is configured for compatibility with an optical reaction module. In one embodiment, the optical reaction module is a differential scanning fluorimeter. In one embodiment, the optical reaction module is configured with an optically readable storage medium device. In one embodiment, the first buffer includes, but is not limited to, MES, citrate and/or cacodylate. In one embodiment, the second buffer includes, but is not limited to, bis-tris propane, bicine and/or HEPES. In one embodiment, the first buffer is at a concentration of 100 mM. In one embodiment, the second buffer is at a concentration of 100 mM. In one embodiment, the different ethylene glycol concentration ranges between approximately 5-30%. In one embodiment, the different ethylene glycol concentration is 5%. In one embodiment, the different ethylene glycol concentration is 10%. In one embodiment, the different ethylene glycol concentration is 15%. In one embodiment, the different ethylene glycol concentration is 20%. In one embodiment, the different ethylene glycol concentration is 25%. In one embodiment, the different ethylene glycol concentration is 30%. In one embodiment, the different 2-methyl-2,4-pentanediol concentration ranges between approximately 2.5-25%. In one embodiment, the different 2-methyl-2,4-pentanediol concentration is 2.5%. In one embodiment, the different 2-methyl-2,4-pentanediol concentration is 5%. In one embodiment, the different 2-methyl-2,4-pentanediol concentration 10%. In one embodiment, the different 2-methyl-2,4-pentanediol concentration is 15%. In one embodiment, the different 2-methyl-2,4-pentanediol concentration is 20%. In one embodiment, the different 2-methyl-2,4-pentanediol concentration is 30%. In one embodiment, the different ethanol concentration ranges between approximately 2.5-25%. In one embodiment, the different ethanol concentration is 2.5%. In one embodiment, the different ethanol concentration is 5%. In one embodiment, the different ethanol concentration 10%. In one embodiment, the different ethanol concentration is 15%. In one embodiment, the different ethanol concentration is 20%. In one embodiment, the different ethanol concentration is 30%. In one embodiment, the different 1,6-hexanediol concentration ranges between approximately 0.125-0.75%. In one embodiment, the different 1,6-hexanediol concentration is 0.125%. In one embodiment, the different 1,6-hexanediol concentration is 0.25%. In one embodiment, the different 1,6-hexanediol concentration 0.375%. In one embodiment, the different 1,6-hexanediol concentration is 0.5%. In one embodiment, the different 1,6-hexanediol concentration is 0.625%. In one embodiment, the different 1,6-hexanediol concentration is 0.75%. In one embodiment, the different 1,2-propanediol concentration ranges between approximately 0.125-0.75%. In one embodiment, the different 1,2-propanediol concentration is 0.125%. In one embodiment, the different 1,2-propanediol concentration is 0.25%. In one embodiment, the different 1,2-propanediol concentration 0.375%. In one embodiment, the different 1,2-propanediol concentration is 0.5%. In one embodiment, the different 1,2-propanediol concentration is 0.625%. In one embodiment, the different 1,2-propanediol concentration is 0.75%. In one embodiment, the different polyethylene glycol 300 concentration ranges between approximately 2.5-25%. In one embodiment, the different polyethylene glycol 300 concentration is 2.5%. In one embodiment, the different polyethylene glycol 300 concentration is 5%. In one embodiment, the different polyethylene glycol 300 concentration 10%. In one embodiment, the different polyethylene glycol 300 concentration is 15%. In one embodiment, the different polyethylene glycol 300 concentration is 20%. In one embodiment, the different polyethylene glycol 300 concentration is 30%. In one embodiment, the different polyethylene glycol 3350 MME concentration ranges between approximately 2.5-25%. In one embodiment, the different polyethylene glycol 3350 MME concentration is 2.5%. In one embodiment, the different polyethylene glycol 3350 MME concentration is 5%. In one embodiment, the different polyethylene glycol 3350 MME concentration is 10%. In one embodiment, the different polyethylene glycol 3350 MME concentration is 15%. In one embodiment, the different polyethylene glycol 3350 MME concentration is 20%. In one embodiment, the different polyethylene glycol 3350 MME concentration is 30%. In one embodiment, the different polyethylene glycol 6000 concentration ranges between approximately 2.5-25%. In one embodiment, the different polyethylene glycol 6000 concentration is 2.5%. In one embodiment, the different polyethylene glycol 6000 concentration is 5%. In one embodiment, the different polyethylene glycol 6000 concentration 10%. In one embodiment, the different polyethylene glycol 6000 concentration is 15%. In one embodiment, the different polyethylene glycol 6000 concentration is 20%. In one embodiment, the different polyethylene glycol 6000 concentration is 30%. In one embodiment, the different polyethylene glycol 10000 concentration ranges between approximately 2.5-25%. In one embodiment, the different polyethylene glycol 10000 concentration is 2.5%. In one embodiment, the different polyethylene glycol 10000 concentration is 5%. In one embodiment, the different polyethylene glycol 10000 concentration 10%. In one embodiment, the different polyethylene glycol 10000 concentration is 15%. In one embodiment, the different polyethylene glycol 10000 concentration is 20%. In one embodiment, the different polyethylene glycol 10000 concentration is 30%. In one embodiment, the different xylitol concentration ranges between approximately 5-30%. In one embodiment, the different xylitol concentration is 5%. In one embodiment, the different xylitol concentration is 10%. In one embodiment, the different xylitol concentration 15%. In one embodiment, the different xylitol concentration is 20%. In one embodiment, the different xylitol concentration is 25%. In one embodiment, the different xylitol concentration is 30%. In one embodiment, the different sucrose concentration ranges between approximately 5-30%. In one embodiment, the different sucrose concentration is 5%. In one embodiment, the different sucrose concentration is 10%. In one embodiment, the different sucrose concentration 15%. In one embodiment, the different sucrose concentration is 20%. In one embodiment, the different sucrose concentration is 25%. In one embodiment, the different sucrose concentration is 30%. In one embodiment, the different trehalose dihydrate concentration ranges between approximately 5-30%. In one embodiment, the different trehalose dihydrate concentration is 5%. In one embodiment, the different trehalose dihydrate concentration is 10%. In one embodiment, the different trehalose dihydrate concentration 15%. In one embodiment, the different trehalose dihydrate concentration is 20%. In one embodiment, the different trehalose dihydrate concentration is 25%. In one embodiment, the different trehalose dihydrate concentration is 30%. In one embodiment, the different erythritol concentration ranges between approximately 5-30%. In one embodiment, the different erythritol concentration is 5%. In one embodiment, the different erythritol concentration is 10%. In one embodiment, the different erythritol concentration 15%. In one embodiment, the different erythritol concentration is 20%. In one embodiment, the different erythritol e concentration is 25%. In one embodiment, the different erythritol concentration is 30%. In one embodiment, the different sodium malonate concentration ranges between approximately 0.25-1.5%. In one embodiment, the different sodium malonate concentration is 0.25%. In one embodiment, the different sodium malonate concentration is 0.5%. In one embodiment, the different sodium malonate concentration 0.75%. In one embodiment, the different sodium malonate concentration is 1%. In one embodiment, the different sodium malonate concentration is 1.25%. In one embodiment, the different sodium malonate concentration is 1.5%. In one embodiment, the different glycerol concentration ranges between approximately 2.5-50%. In one embodiment, the different glycerol concentration is 2.5%. In one embodiment, the different glycerol concentration is 5%. In one embodiment, the different glycerol concentration 10%. In one embodiment, the different glycerol concentration is 15%. In one embodiment, the different glycerol concentration is 20%. In one embodiment, the different glycerol concentration is 25%. In one embodiment, the different glycerol concentration is 30%. In one embodiment, the different glycerol concentration is 35%. In one embodiment, the different glycerol concentration is 40%. In one embodiment, the different glycerol concentration is 45%. In one embodiment, the different glycerol concentration is 50%.

In one embodiment, the present invention contemplates a device, comprising:
  a) a solid substrate comprising a plurality of testing wells and a control well, wherein each of said plurality of testing wells comprises a first buffer and a second buffer, said control well comprises a sample buffer, and each of said testing wells and control well comprises a protein sample;
  b) a first testing well series of said plurality of testing wells comprising a first hydrogen ion concentration, wherein each well of said first testing well series comprises a different sodium chloride concentration;
  c) a second testing well series of said plurality of testing wells comprising a second hydrogen ion concentration, wherein each well of said second testing well series comprises a different sodium chloride concentration;
  d) a third testing well series of said plurality of testing wells comprising a third hydrogen ion concentration, wherein each well of said third testing well series comprises a different sodium chloride concentration;
  e) a fourth testing well series of said plurality of testing wells comprising a fourth hydrogen ion concentration, wherein each well of said fourth testing well series comprises a different sodium chloride concentration;
  f) a fifth testing well series of said plurality of testing wells comprising a fifth hydrogen ion concentration, wherein each well of said fifth testing well series comprises a different sodium chloride concentration;
  g) a sixth testing well series of said plurality of testing wells comprising a sixth hydrogen ion concentration, wherein each well of said sixth testing well series comprises a different sodium chloride concentration;
  h) a seventh testing well series of said plurality of testing wells comprising a seventh hydrogen ion concentration, wherein each well of said seventh testing well series comprises a different sodium chloride concentration;
  i) an eighth testing well series of said plurality of testing wells comprising an eighth hydrogen ion concentration, wherein each well of said eighth testing well series comprises a different sodium chloride concentration; and
  j) a ninth testing well series of said plurality of testing wells comprising a ninth hydrogen ion concentration, wherein each well of said ninth testing well series comprises a different sodium chloride concentration.

In one embodiment, the device is configured for compatibility with a thermocycler. In one embodiment, the thermocycler is a real time thermocycler. In one embodiment, the thermocycler is configured for compatibility with an optical reaction module. In one embodiment, the optical reaction module is a differential scanning fluorimeter. In one embodiment, the optical reaction module is configured with an optically readable storage medium device. In one embodiment, the first buffer includes, but is not limited to, MES, citrate and/or cacodylate. In one embodiment, the second buffer includes, but is not limited to, bis-tris propane, bicine and/or HEPES. In one embodiment, the first buffer is at a concentration of 100 mM. In one embodiment, the second buffer is at a concentration of 100 mM. In one embodiment, the first hydrogen ion concentration has a pH 5.0. In one embodiment, the second hydrogen ion concentration has a pH 5.5. In one embodiment, the third hydrogen ion concentration has a pH 6.0. In one embodiment, the fourth hydrogen ion concentration has a pH 6.5. In one embodiment, the fifth hydrogen ion concentration has a pH 7.0. In one embodiment, the sixth hydrogen ion concentration has a pH 7.5. In one embodiment, the seventh hydrogen ion concentration has a pH 8.0. In one embodiment, the eighth hydrogen ion concentration has a pH 8.5. In one embodiment, the ninth hydrogen ion concentration has a pH 9.0. In one embodiment, the first buffer is 2-(N-morpholino)ethansulfonic acid. In one embodiment, the second buffer is bis-tris propane. In one embodiment, the different sodium chloride concentration ranges between approximately 0.125 M-1.0 M. In one embodiment, the different sodium chloride concentration includes, but is not limited to, 0.125 M, 0.25 M, 0.5 M, 0.75 M, and/or 1.0 M.

In one embodiment, the present invention contemplates a method for designing a customized protein-specific buffer system, comprising: a) providing: i) a solid substrate comprising a plurality of testing wells and a control well, wherein each of said plurality of testing wells comprises a first buffer and a second buffer and a different test compound, said control well comprises a sample buffer, and each of said plurality of testing wells and control well comprises a protein sample; and ii) a thermocycler device configured with an optical reaction module and an optically readable storage medium device; b) inserting the solid substrate into said thermocycler device; c) cycling the thermocycler device between a first temperature and a second temperature under conditions such that the optical reaction module generates a data file from each of said plurality of testing well series and control well; d) storing the data files on said optically readable storage medium device; and e) processing said data files to select at least one test compound as a component for a customized buffer system for said protein. In one embodiment, the processing produces a plurality of protein melting point temperature profiles. In one embodiment, the protein melting point temperature profiles comprise an inflection point. In one embodiment, the selected at least one test compound has a higher inflection point $T_m$ than the control inflection point $T_m$. In one embodiment, the customized buffer system maximizes conformation stability of said protein. In one embodiment, the customized buffer system maximizes cryoprotection of said protein. In one embodiment, the first buffer includes, but is not limited to, MES, citrate and/or cacodylate. In one embodiment, the second buffer includes, but is not limited to, bis-tris propane, bicine and/or HEPES. In one embodiment, the different test compound is ammonium sulphate. In one embodiment, the different test compound is an amino acid. In one embodiment, the different test compound is urea. In one embodiment, the different test compound is glycerol. In one embodiment, the different test compound is a hydrogen ion. In one embodiment, the different test compound is a third buffer. In one embodiment, the different test compound is dimethyl sulfoxide. In one embodiment, the different test compound is a Hoefmeister Series compound. In one embodiment, the different test compound is a metal ion. In one embodiment, the different test compound is ethylene glycol. In one embodiment, the different test compound is polyethylene glycol 3350. In one embodiment, the different test compound is erythritol. In one embodiment, the different test compound is 2-methyl-2,4-pentanediol. In one embodiment, the different test compound is polyethylene glycol 6000. In one embodiment, the different test compound is sodium malonate. In one embodiment, the different test compound is ethanol. In one embodiment, the different test compound is polyethylene glycol 10,000. In one embodiment, the different test compound is glycerol. In one embodiment, the different test compound is xylitol. In one embodiment, the different test compound is sucrose. In one embodiment, the different test compound is trehalose dihydrate. In one embodiment the different test compound is 1,6 hexanediol. In one embodiment, the different test compound is sodium chloride. In one embodiment, the different third buffer includes, but is not limited to, Trizma, HEPES, Pipes, Bicine, Bis-Tris, TES, MOPS, MES, PBS, CAPS, CHES, Bis-Tris Propane and TAPS.

In one embodiment, the present invention contemplates a method for determining protein quality: comprising: a) providing; i) a solid substrate comprising a plurality of testing wells and a control well, wherein each of said plurality of testing wells are prefilled with a first buffer and a second buffer, and a plurality of testing well series of said plurality of testing wells wherein each well of said plurality of testing well series is prefilled with a different hydrogen ion concentration; and ii) a thermocycler device configured with an optical reaction module and an optically readable storage medium device; b) inserting the solid substrate into said thermocycler device; c) cycling the thermocycler device between a first temperature and a second temperature under conditions such that the optical reaction module generates a data file from each of said plurality of testing well series and control well; d) storing the data files on said optically readable storage medium device; e) processing said data files to produce a plurality of protein melting point temperature profiles; f) displaying said protein melting point temperature profiles as a first three dimensional map; and g) identifying changes in quality of said protein by differences between the first three dimensional map to a control three dimensional map of said protein. In one embodiment, each well of said plurality of testing well series further comprises a different sodium chloride concentration. In one embodiment, the first buffer includes, but is not limited to, MES, citrate and/or cacodylate. In one embodiment, the second buffer includes, but is not limited to, bis-tris propane, bicine and/or HEPES. In one embodiment, the device is compatible with a thermocycler configured with an optical reaction module and an optically readable storage medium device.

In one embodiment, the present invention contemplates a protein stability conditions kit, comprising a solid substrate comprising a plurality of testing wells and a control well, wherein each of said plurality of testing wells are prefilled with a first buffer and a second buffer, and a plurality of testing well series of said plurality of testing wells wherein each of said plurality of testing well series is prefilled with a different test compound. In one embodiment, the different test compound is ammonium sulphate. In one embodiment, the different test compound is an amino acid. In one embodiment, the different test compound is urea. In one embodiment, the different test compound is glycerol. In one embodiment, the different test compound is a hydrogen ion. In one embodiment, the different test compound is a third buffer. In one embodiment, the different test compound is dimethyl sulfoxide. In one embodiment, the different test compound is a Hoefmeister Series compound. In one embodiment, the different test compound is a metal ion. In one embodiment, the first buffer includes, but is not limited to, MES, citrate and/or cacodylate. In one embodiment, the second buffer includes, but is not limited to, bis-tris propane, bicine and/or HEPES. In one embodiment, the different third buffer includes, but is not limited to, Trizma, HEPES, Pipes, Bicine, Bis-Tris, TES, MOPS, MES, PBS, CAPS, CHES, Bis-Tris Propane and TAPS. In one embodiment, the device is configured for compatibility with a thermocycler. In one embodiment, the thermocycler is compatible with an optical reaction module configured with an optically readable storage medium device.

In one embodiment, the present invention contemplates a protein cryoprotection conditions kit, comprising a solid substrate comprising a plurality of testing wells and a control well, wherein each of said plurality of testing wells are prefilled with a first buffer and a second buffer, and a plurality of testing well series of said plurality of testing wells wherein each of said plurality of testing well series is prefilled with a different test compound. In one embodiment, the different test compound is ethylene glycol. In one embodiment, the different test compound is polyethylene glycol 3350. In one embodiment, the different test compound is erythritol. In one embodiment, the different test compound is 2-methyl-2,4-pentanediol. In one embodiment, the different test compound is polyethylene glycol 6000. In one embodiment, the different test compound is sodium malonate. In one embodiment, the different test compound is ethanol. In one embodiment, the different test compound is polyethylene glycol 10,000. In one embodiment, the different test compound is glycerol. In one embodiment, the different test compound is xylitol. In one embodiment, the different test compound is sucrose. In one embodiment, the different test compound is trehalose dihydrate. In one embodiment the different test compound is 1,6 hexanediol. In one embodiment, the test compound is 1,2 propanediol. In one embodiment, the first buffer includes, but is not limited to, MES, citrate and/or cacodylate. In one embodiment, the second buffer includes, but is not limited to, bis-tris propane, bicine and/or HEPES. In one embodiment, the device is compatible with a thermocycler configured with an optical reaction module and an optically readable storage medium device.

In one embodiment, the present invention contemplates a protein quality control kit, comprising a solid substrate comprising a plurality of testing wells and a control well, wherein each of said plurality of testing wells are prefilled with a first buffer and a second buffer, and a plurality of testing well series of said plurality of testing wells wherein each well of said plurality of testing well series is prefilled with a different hydrogen ion concentration. In one embodiment, each well of said plurality of testing well series further comprises a different sodium chloride concentration. In one embodiment, the first buffer includes, but is not limited to, MES, citrate and/or cacodylate. In one embodiment, the second buffer includes, but is not limited to, bis-tris propane, bicine and/or HEPES. In one embodiment, the device is compatible with a thermocycler configured with an optical reaction module and an optically readable storage medium device.

In one embodiment, the present invention contemplates a physiologic liquid buffer mixture comprising at least two buffers, wherein said mixture has a low specific heat and a stable dissociation constant between 5-9 pH over a temperature range of 0-45° C. In one embodiment, the at least two buffers comprise 2-(N-morpholino)ethansulfonic acid (MES) and bis-tris propane (BTP). In one embodiment, the at least two buffers comprise citrate and bicine. In one embodiment, the at least two buffers comprise cacodylate and HEPES. In one embodiment, the buffer mixture further comprises a third buffer including, but not limited to, N-Cyclohexyl-2-aminoethanesulfonic acid (CHES), Trizma, piperazine-N,N'-bis(2-ethanesulfonic acid (PIPES), Bis-Tris, 2-[[1,3-dihydroxy-2-(hydroxymethyl)propan-2-yl]amino] ethanesulfonic acid (TES), 3-(N-morpholino)propanesulfonic acid (MOPS), phosphate buffered saline (PBS), N-cyclohexyl-3-aminopropanesulfonic acid (CAPS), and/or N-Tris(hydroxymethyl)methyl-3-aminopropanesulfonic acid (TAPS).

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" or "approximately" as used herein, in the context of any of any assay measurements refers to +/−5% of a given measurement.

The term "stability index" as used herein refers to a calculated interpolation between at least two independently collected data sets. For example, a stability index may be calculated by interpolating between protein melting point temperature profiles of concentration-dependent profiles of ammonium sulphate versus urea. This "stability index" allows for the nomination of conditions that simultaneously selects for both maximum protein stability and maximum protein solubility, whereas previous testing methods were only capable of selecting for protein stability.

The term "custom designed", "designed" or "designing" as used herein refers to a method or process that results in the creation of a novel buffer system than has superior and optimal properties of a specific protein. Such superior and optimal properties are determined by an empirical testing process, as described herein, such that any identified custom designed buffer composition could not be predicted on an a priori basis.

The terms "arrays" and "microarrays" are used somewhat interchangeably differing only in general size. The instant invention involves the same methods for making and using either. Each array typically contains many wells (typically 96 or a multiple thereof) wherein each well is at a known location and contains specific components of interest. Each array therefore contains numerous different components of interest.

In a related aspect, the terms "plate" or "device" are used to describe both arrays and microarrays, where the array or microarray may comprise other defined components including surfaces and points of contact between reagents.

Further, "substrate" or "solid substrate" is also a term used to describe surfaces as well as solid phases which may comprise the array, microarray, plate or device. In some cases, the substrate is solid and may include, but is not limited to, glass, plastic, silicon and/or PDMS.

The term "buffer" as used herein, refers to an aqueous solution consisting of a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of chemical applications.

The term "buffer mixture" or "buffer system" as used herein, refers to an aqueous solution consisting of a mixture of at least two weak acids and their conjugate base, or vice versa. The mixture pH changes very little over a wide temperature range (e.g., for example, 1-70° C.) due to buffer-buffer interactions that maintain an overall balanced buffer mixture/system pKa. A buffer mixture/system may also contain other components including, but not limited to, salts, ions, metals and/or supplemental buffer molecules.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term, "purified" or "isolated", as used herein, may refer to a peptide composition that has been subjected to treatment (i.e., for example, fractionation) to remove various other components, and which composition substantially retains its expressed biological activity.

Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that all trace impurities have been removed.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a biological and/or environmental sample may comprise proteins derived from a cell, tissue extract and/or body fluid.

As used herein, the term "Tm" is used in reference to a protein "melting temperature." The melting temperature is the temperature at which a population of isolated proteins denature and/or unfold from a quaternary and/or tertiary conformation into a primary and/or secondary conformation.

The term "marker", "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "luminescence" and/or "fluorescence", as used herein, refers to any process of emitting electromagnetic radiation (light) from an object, chemical and/or compound. Luminescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

BRIEF DESCRIPTION OF THE FIGURES

FIG. 16A: Concentration-dependent protein destabilization effects of urea.

FIG. 16B: Concentration-dependent protein stabilization effects of ammonium sulphate.

FIG. 17 presents exemplary data showing the relative stability of protein melting point temperatures over a wide pH range. The present data were collected with the Dwarf27 protein (D27)

FIG. 17A: pH-dependent protein melting point screen using a single component sodium phosphate buffer.

FIG. 17B: pH-dependent protein melting temperature point screen using a multi-component MES/BTP buffer system.

DETAILED DESCRIPTION OF THE INVENTION

Figure 1:
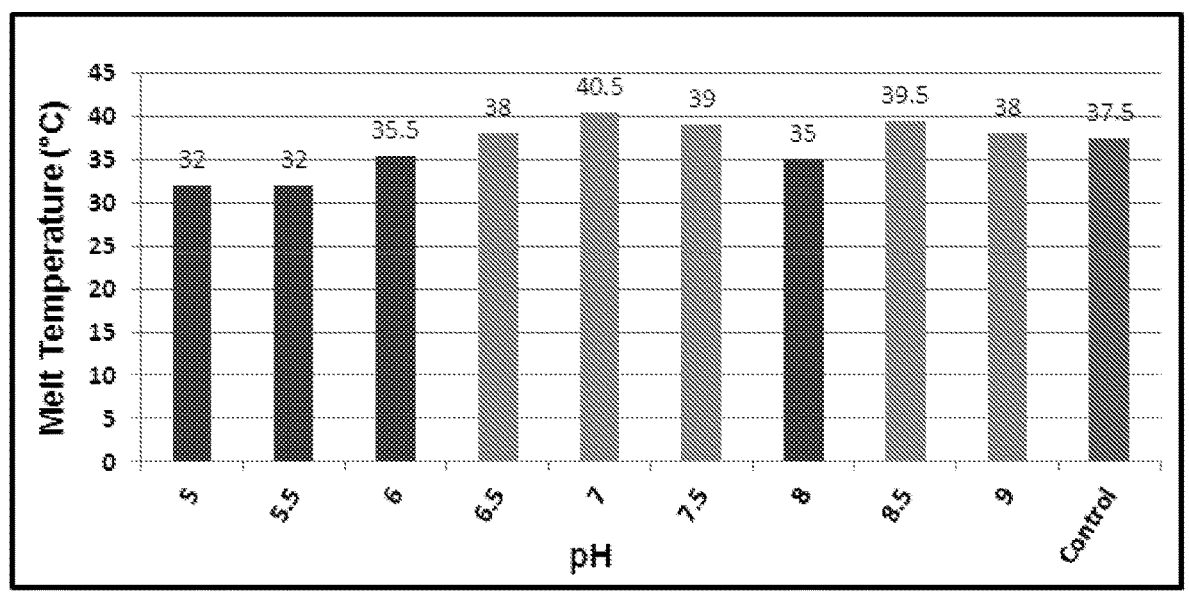
FIG. 1 presents exemplary data showing a protein temperature melting point profile in a MES/BTP buffer over a pH range between 5-9.

The present invention is related to the field of protein chemistry. In particular, mixed buffer compositions are formulated that allow an accurate identification of agent-induced changes in protein melting point temperatures. Such mixed buffer compositions provide for methods that determine the specific effects of exogenous agents on protein stability, cryoprotective effects and/or protein quality control (e.g., for synthesis and/or extraction purity validations). Optimal exogenous agents are then selected for inclusion into customized buffer systems that are protein-specific.

In one embodiment, the present invention contemplates series of protein melting point temperature screens that can be used to define an optimal biochemical composition for various types of proteomic buffer mixture systems. In one embodiment, the optimal biochemical composition is designed to improve protein stability. In one embodiment, the optimal biochemical composition is designed to improve protein cryoprotection. In one embodiment, the optimal biochemical composition is designed to provide improved protein quality control data.

Although it is not necessary to understand the mechanism of an invention, it is believed that the basic chemistry of the compositions and methods contemplated herein have a technological foundation that is implemented in various ways including, but not limited to: i) plate well layout and compositions; 2) nomination (e.g., selection) of test compounds compatible with heating; iii) use of internal standards; and iv) a multi-component buffered solution (e.g., for example, a physiological buffer mixture) that enables a stable measure of pH at various temperatures. For example, it has been reported that the binding of low molecular weight ligands can increase the thermal stability of a protein. Koshland, D E (1958). "Application of a Theory of Enzyme Specificity to Protein Synthesis". Proceedings of the National Academy of Sciences of the United States of America 44 (2): 98-104; and Linderstrøm-Lang et al., (1959). "Protein structure and enzyme activity". The Enzymes 1(2) 443-510.

In general, the methods contemplated herein can be performed, in part, by using commercially available quantitative polymerase chain reaction (qPCR) thermocycler instruments to increase the temperature of a proteomic sample and monitoring protein unfolding by dye binding. To date, there have been many companies that produce and sell instruments created to facilitate these types of measurements including, but not limited to: i) Evacta Analytical: Optim 2; ii) NanoTemper Technology: Prometheus NT.48; iii) Roche; iv) BioRad; v) Applied Biosystems; and vi) Stratagene/Agilent. While these instruments are validated for testing generalized protein stability characteristics, these instruments were not validated to provide specific data that can be used to select buffer components for a custom designed protein-specific buffer system.

Although it is not necessary to understand the mechanism of an invention, it is believed that protein crystallization is more successful for proteins with a higher melting point and adding buffer components that stabilize proteins will improve the likelihood of protein crystals forming. It is further believed that by examining buffer mixture pH, the possible effects of buffer molecules on thermal stability are taken into account along with the fact that pKa of each buffer molecule changes uniquely with temperature, thereby inherently inducing buffer pH changes. In one embodiment, the present invention contemplates a method comprising a protein thermal melting screen that optimizes the foundation chemistry required to accurately measure the pH of a buffered protein mixture under heated conditions.

The data presented herein identify chemistries have been formulated for use in the biochemical analysis of proteins using methods referred to as either Thermal Melting Analysis (TMA) or Thermal Stability Analysis (TSA). In general, the methods contemplated herein may be performed in a standard array platform (e.g., for example, a 96 well format) but one of ordinary skill would understand that higher order screening kits (e.g. for example, a 384 well format, a 768 well format, and/or a 1536 well format) are also compatible with the presently disclosed methods. Such high throughput assay platforms allow this technology to test thousands of test compounds per hour.

In one embodiment, the present invention contemplates methods where a single buffer mixture (e.g., for example, MES and BTP) is used in all protein melting point temperature screens which are formulated to contain only one changing variable per well across the entire temperature scan spectrum. For example, a glycerol screen may be performed at various concentrations (e.g., for example 5%, 10%, 15%) where a buffer mixture composition is identical for all measurements at every temperature. In other words, all other buffer components remain unchanged so that the analysis is a reflection of only that one parameter.

In one embodiment, the present invention contemplates a method to determine a custom designed physiologic liquid buffer mixture for a specific protein, by identifying screening specific buffer parameters to identify changes in protein $T_m$ as the temperature scan proceeds from lower temperatures to higher temperatures.

Further, a single buffer mixture used for the test compound screens generally have characteristics including, but not limited to: i) a low specific heat (e.g., $\Delta C_P$); ii) decreased chelation effects; iii) reduced buffer-buffer interactions; iv) minimal ion interactions; v) decreased interaction between buffers and other reactive components; and vi) minimal effects on dissociation from changes in temperature and concentration. For example, buffer mixtures meeting these characteristics include, but are not limited to: i) MES/Bis-Tris Propane; ii) citrate/bicine; and iii) Cacodylate+HEPES. These representative physiologic liquid buffer mixtures are useful in determining, for example, the specific effect of various test compounds on protein melting point temperature. Alternatively, the methods presently contemplated herein provide that the single buffer mixture that can identify optimal supplemental buffers at different pH's (e.g., for example, at pH 7 and pH 9) for inclusion into a customized protein-specific buffer system.

Preliminary data (not shown) have provided for the analysis of thousands of proteins using the methods described herein and have identified numerous protein sample parameters for performing these methods. For example: i) minimum sample size (0.5 mg/mL); ii) protein molecular weight >10K Da; iii) protein sample volume (10 µL); iv) protein sample purity (>85%). For example, screens have been performed for proteins including, but not limited to, Dwarf27, MX-4, ABL-1, ASH-2L, BACE1, BRD-1, BRD-2, C3, CHD1, COMT, ECT2, eIF4E, FIH, FABP4, HMG CoA Reductase, IDH1, JMJD2A, KRAS, L3MBTL1, LoxL2, Menin, MX4, NNMT, NSD3, rhPCSK9, SET 7-9, SIRT6, SMYD1, SMYD2, STING, TAF1, Tip60, TPH1, UTX, and VDR.

I. Conventional Buffer Systems for Protein Melting Point Temperature Determination Buffer mixtures have been reported consisting of a first buffer (pH=6-10) such as, BTP or bicine with a second buffer (pH=6-9) including phosphate, citrate, MES, PIPES, MOPS, TES, cacodylate, HEPES, and Bis-Tris, wherein the second buffer may be any combination and in concentrations ranging from about 10 mM to about 1.5 M. It was not suggested or taught that these buffer mixtures have a low specific heat and/or a stable dissociation constant between 0-40° C. Diller et al., "Rapid Protein Labeling And Analysis" U.S. Pat. No. 8,609,423 (herein incorporated by reference).

Solutions have been reported consisting of one or more of the following buffers: Tris, bis-Tris, bis-Tris propane, MES, phosphate, cacodylate, HEPES, MOPS, TAPS, citrate, bicine, Tricine, TES and/or PIPES at concentration ranges between 20-500 mM. It was not suggested or taught that these buffer mixtures have a low specific heat and/or a stable dissociation constant between 0-40° C. Frauenschuh A., "Purification Method For Proteins, In Particular Antibodies, Utilizing A Wash Solution Comprising Arginine At High pH For The Affinity Chromatography Step" United States Patent Application Publication No. 2014/0094593 (herein incorporated by reference).

Mixtures of at least two buffers have been reported where one buffer has a positive temperature coefficient and the other buffer has a negative temperature coefficient within the same temperature range. For example, the temperature dependence of pH levels were measured in 75% glycerol solutions containing a buffer mixture of 4-(2-hydroxyethyl)-1-piperazineethanesulfonate (HEPES) buffer and potassium phosphate (KPhosphate) buffer or a buffer mixture of Bis-Tris Propane (BTP) buffer and KPhosphate buffer. Examples of a positive temperature coefficient buffer includes phosphate. Examples of negative temperature coefficient buffers include MOPS, Tris, 2-[bis(2-hydroxyethyl)amino]-2-(hydroxymethyl)propane-1,3-diol (BisTris), BisTrisPropane (BTP), 2-Morpholinoethanesulfonic (MES), and HEPES. It was reported that the pH stability of such mixtures had a variability of between 0.25-1.0 pH unit and contemplates that buffer systems would preferably display the smallest change of pH as a function of temperature for a defined temperature range. Nonetheless, a buffer mixture having a low specific heat and a stable dissociation constant between 0-40° C. was neither suggested nor taught. A buffer mixture comprising either citrate+bicine or cacodylate+HEPES was also not taught. Lu et al., "Temperature Resistant pH Buffers For Use At Low Temperatures" United States Patent Application Publication Number 2008/0171393 (herein incorporated by reference).

Protein melting point temperatures have been determined between 303-373° K (30-100° C.) by using different buffers at different pH's consisting of MES (pH 5.8), HEPES (pH 6.8) and Bis-Tris Propane (pH 7.8). Use of identical buffer mixtures were not suggested or disclosed to provide protein melting point temperature at different pH's. A buffer mixture was further not suggested nor taught that had a low specific heat and a stable dissociation constant between 0-40° C. A buffer mixture comprising either citrate+bicine or cacodylate+HEPES was also not taught. Luft et al., "Crystal Cookery—Using High-Throughput Technologies And The Grocery Store As A Teaching Tool" *Journal of Applied Crystallography* 43:1189-1207 (2010).

Tryptophan hydroxylase (TH) melting point temperatures were determined using differential scanning fluorimetry (DSF) using the following buffers: i) 10 mM HEPES/NaOH (pH 7.0); or ii) 20 mM Tris/$H_2SO_4$ and 300 mM $(NH_4)_2SO_4$ (pH 8.0). DSF assays to determine the optimal pH for TH stability were performed within a range of between pH 6-9 using a buffer combination of 22 mM citric acid, 33 mM HEPES, 44 mM 2-(Cyclohexylamino)ethanesulfonic acid (CHES)/NaOH and 300 mM $(NH_4)_2SO_4$ over a temperature range of 35-65° C. (FIG. 36). The TH melting points at pH 5 and pH 10 were unable to be determined because of protein precipitation. DSF determination of the effect of various salts on optimal pH for TH stability used a buffer of 100 mM Tris/$H_2SO_4$ or HCl (pH 8.0) over a temperature range of 35-65° C. (FIG. 37). DSF determination of the effect of ammonium sulphate on optimal pH for TH stability used a buffer of 100 mM Tris/$H_2SO_4$ (pH 8.0) over a temperature range of 35-65° C. (FIG. 38). The melting/unfolding temperature of TH variants were tested in a pH range from 5.0-9.0 over a temperature range of 35-65° C. using a citric acid/HEPES/CHES buffer combination with 300 mM $(NH_4)_2SO_4$ (FIG. 55). TH melting temperatures were tested in the presence of various salts using a 20 mM HEPES/NaOH buffer (pH 7.0) in comparison with $(NH_4)_2SO_4$ (See, FIGS. 56 and 57). While it was suggested that a buffer system and/or buffer concentration might be expected to have some effects on the TH melting temperature that is independent of pH and salt concentration, three different buffers (HEPES, Bis Tris Propane and 3-(N-morpholino)propanesulfonic acid (MOPS)) were tested at same pH and salt concentration but showed no significant effect on stability. Typical protein stabilizing molecules (e.g., glycerol, sucrose, polyethylene glycol (PEG) 400 and sorbitol) were studied and gave an increased melting temperature using a buffer of 20 mM HEPES/NaOH and 100 mM $(NH_4)_2SO_4$ (pH 7.0). It was neither suggested nor taught to use a buffer mixture having a low specific heat and a stable dissociation constant between 0-40° C. A buffer mixture comprising either citrate+bicine or cacodylate+HEPES was also not taught. Haahr L. T., "Purification and Characterization of Tryptophan Hydroxylase" Doctorate Of Philosophy Thesis, Metalloprotein Chemistry & Engineering, DTU Chemistry, Technical University of Denmark (2012).

A buffer mixture of MES, HEPES and CHES was studied for its buffering capacity at 20° C. in comparison to a respective "ionic liquid" mixture. It was recommended that Good's Buffers be used as starting materials for the synthesis of "ionic liquid buffers". It was suggested that because enzyme activity spans a wide pH range, different buffers should be used to cover the entire pH range. Single buffering solutions were suggested that had a broad working pH range that would greatly simplify the interpretation of enzyme activity data and pointed out that there are few useful universal-buffers because most physiologic buffers interact with proteins or chelate metal ions. MES, HEPES, and CHES were suggested as potential buffers that might have negligible metal-binding affinity and would make them suitable for formulating biocompatible universal single buffers. A buffer mixture having a low specific heat and a stable dissociation constant between 0-40° C. was neither suggested nor taught. Further, a buffer mixture comprising either citrate+bicine or cacodylate+HEPES was also not taught. Taha et al., "Good's Buffers As A Basis For Developing Self-Buffering And Biocompatible Ionic Liquids For Biological Research" Green Chem. 16(6):3149-3159 (2014) An aqueous mixture has been reported that comprises two or more buffers, wherein the buffers may include, phosphate, MES, Bis-Tris, Tri-Bis Propane, PIPES and/or Tris at concentrations of about 0.1 M to about 2.0 M. Nonetheless, there is no teaching or suggestion to use any specific buffer mixture to perform protein melting point temperature screens. As such, there is no suggestion or teaching of a buffer mixture having a low specific heat and a stable dissociation constant between 0-40° C. A buffer mixture comprising either citrate+bicine or cacodylate+HEPES is also not taught. Motheram R., "Buffer-Based Method For Preparing Bivalirudin Drug Product" U.S. Pat. No. 7,985,733 (herein incorporated by reference).

Buffer mixtures have been reported comprising one or more buffers including $K_2HPO_4$, $KH_2PO_4$, Bis Tris, Bis-Tris Propane, HEPES, Trizma, Tris base, Tricine, Bicine, PIPES, MOPS, TES, TAPS, CHES, CAPS, MES in mixtures of two or more thereof at concentrations ranging between 0.1-1000 g/L. Nonetheless, there is no teaching or suggestion to use any specific buffer mixture to perform protein melting point temperature screens. As such, there is no suggestion or teaching of a buffer mixture having a low specific heat and a stable dissociation constant between 0-40° C. A buffer mixture comprising either citrate+bicine or cacodylate+HEPES is also not taught. Franciskovich et al., "Methods For Making A Sterilization Indicator And For Monitoring A Sterilization Process Using Membrane Potential" U.S. Pat. No. 9,012,173 (herein incorporated by reference).

A background electrolyte composition was disclosed for analyzing trace iron in water comprising morpholinoethanesulfonic acid (MES) and bis-tris propane (pH 6.6). Nonetheless, there is no teaching or suggestion to use any specific buffer mixture to perform protein melting point temperature screens. As such, there is no suggestion or teaching of a buffer mixture having a low specific heat and a stable dissociation constant between 0-40° C. A buffer mixture comprising either citrate+bicine or cacodylate+HEPES is also not taught. Blanty et al., "Trace Determination Of Iron In Water At the Microgram/1 Level By On-Line Coupling Of Capillary Isotachophoresis And Capillary Zone Electrophoresis With UV Detection Of the EDTA-Fe (III) Complex" J. Chromatogr A 757:297-302 (1997)

MES acid anions and bis-tris propane, as background electrolytes, were reported to differentially affect alkaloid mobility due to cation ion pairing with anionic analytes. Nonetheless, there is no teaching or suggestion to use any specific buffer mixture to perform protein melting point temperature screens. As such, there is no suggestion or teaching of a buffer mixture having a low specific heat and a stable dissociation constant between 0-40° C. A buffer mixture comprising either citrate+bicine or cacodylate+HEPES is also not taught. Vespalec et al., "Aggregation And Other Intermolecular Interactions Of Biological Buffers Observed By Capillary Electrophoresis And UV Photometry" J. Chromatogr A 1051:75-84 (2004)

A protein melting temperature screening assay has been reported that was performed using a 96 well plate and each well contains a different composition. However, assay evaluated singly the effects of twenty-three different buffers at different pH's. At no point was it suggested or taught to use buffer mixtures in any of the testing wells to determine protein melting point temperatures. It was also not suggested nor taught that these buffers have a low specific heat and a stable dissociation constant between 0-40° C. Reinhard et al., "Optimization of protein buffer cocktails using Thermofluor" Acta Crystallographica Section F Structural Biology and Crystallization Communications 69:209-214 (2013)

II. Stable $pK_a$ Mixed Buffer Compositions

The effect of temperature on solution pH can be simulated by computer (i.e., for example, PHTEMP®). It has been determined that the change in pH due to shifts in acid-base equilibria [$\Delta pH=pH(60°\ C.)-pH(25°\ C.)$] can be substantial for compounds such as aliphatic amines that have high enthalpies for acid dissociation. This may be of particular significance during elevated temperature experiments (e.g., for example, protein melting point temperature determinations) in which changes in the pKa values of formulation components, and hence the solution pH, can accelerate decomposition as compared to those formulations where sensitive functionality is absent. Computer programs such as PHTEMP® afford exemplary results at an initial pH=7 (25° C.): (a) 0.1 M triethylamine ($\Delta H$ zero=10.4 kcal/mol) $\Delta pH$ approximately −0.8; (b) 0.1 M acetic acid ($\Delta H$ zero=−0.1 kcal/mol) $\Delta pH$ approximately 0; (c) 0.1 M sulfuric acid ($\Delta H$ zero 1=−12 kcal/mol; $\Delta H$ zero 2=−5.4 kcal/mol) $\Delta pH$ approximately −0.4. Solutions of general pharmaceutical interest were also studied and included a 12-component amino acid mixture, 0.1 M glycine, and 0.1 M triethylamine in either 0.02 M citric acid or 0.05 M TRIS buffer. In each case the pH change with temperature was dependent on the concentrations of components, the enthalpies for each acid dissociation, and the starting pH. At lower pH (i.e., for example, <4), PHTEMP® predicts that $\Delta pH$ is typically smaller than at higher pH (i.e, for example, >9). These results may be interpreted as the effect of a relative change in hydronium ion activity, $\Delta H^+/H^+_{(initial)}$, due to temperature-induced shifts in equilibria (i.e., for example, acid dissociation and/or water autoprotolysis). This relative change may become larger as $H^+$ decreases and pH concomitantly increases. The output of PHTEMP® was experimentally verified with 0.1 M glycine and with a multiple component amino acid solution. These results suggest that formulation choices may be assessed for both thermodynamic and traditional kinetic effects on the resulting product stability. Kipp et al., "Computer simulation of the effect of temperature on pH" *J Pharm Sci.* 84(11):1347-1352 (1995).

The knowledge of the acid-base equilibria in water-solvent mixtures of both common buffers and analytes can be used in order to predict their retention as function of pH, solvent composition and temperature. Effects of temperature on acid-base equilibria in methanol-water solvent mixtures commonly used as HPLC mobile phases have been reported. For example, delta-correction parameter (delta=sw pH−ss pH=Ej−log sw(gamma)oh) were measured between two pH scales: pH measured in the solvent concerned and referred to the same standard state, ss pH, and the pH measured in that solvent mixture but referred to water as standard state, sw pH, for several methanol compositions in the temperature range of 20-50 degrees C. These determinations suggest that the delta-term may depend on composition of the mixture and on temperature. In water-rich mixtures, for which methanol is below 40% (w/w), delta-term seems to be independent of temperature, within the experimental uncertainties, whereas for methanol content larger than 50% (w/w) the delta-correction decreases as temperature increases. This decrease may be attributed to a large increase in the medium effect when mixtures have more than 50% methanol. The pKa of five weak electrolytes of different chemical nature in 50% methanol-water at 20-50 degrees C. were differentially effected. For example, the effect of temperature on pKa was large for amines, pyridine and phenol, but almost no dependence was found for benzoic acid. This indicates that buffers can play a role in affecting retention and selectivity in HPLC at temperatures far from 25 degrees C., particularly for co-eluted solutes. Castells et al., "Effect of temperature on pH measurements and acid-base equilibria in methanol-water mixtures" *J Chromatogr A.* 1002(1-2): 41-53 (2003).

In one embodiment, the present invention contemplates mixed buffer compositions that are stable over a wide range of temperatures to evaluate protein melting point stability, cryopreservation efficiency, and protein production quality control. Current conventional protein buffers have the disadvantage that changes in incubation temperature inherently change the physical parameters of a buffer molecule thereby providing an uncontrolled variable in observed protein melting temperatures. As disclosed in the present invention, these buffer mixtures reduce the impact of temperature-induced changes in buffer molecule physical parameters such that the observed changes in protein physical parameters can be attributed only to changes in temperature, and not due to changes in buffer characteristics. One particular advantage of the present method is that these disclosed buffer mixture permits a protein melting point temperature scan to be performed in all pH conditions using the same buffer mixture.

In one embodiment, the present invention contemplates compositions comprising mixtures of physiological buffers including, but not limited to, 2-(N-morpholino)ethanesulfonic acid (MES), Bis-Tris Propane (BTP), N-Cyclohexyl-2-aminoethanesulfonic acid (CHES), Trizma, 4-(2-hydroxyethyl)-1-piperazine ethanesulfonic acid (HEPES), piperazine-N,N'-bis(2-ethanesulfonic acid (PIPES), Bicine, Bis-Tris, 2-[[1,3-dihydroxy-2-(hydroxymethyl)propan-2-yl]amino]ethanesulfonic acid (TES), 3-(N-morpholino)propanesulfonic acid (MOPS), phosphate buffered saline (PBS), N-cyclohexyl-3-aminopropanesulfonic acid (CAPS), N-Tris(hydroxymethyl)methyl-3-aminopropanesulfonic acid (TAPS), citrate and cacodylate. Such buffers may be combined in any number, amount and/or relative concentrations. Advantages of these mixed buffer compositions include, but are not limited to, having a low specific heat and/or a stable dissociation constant between 5-9 pH over a temperature range of 0-45° C. In one embodiment, a buffer mixture comprises 2-(N-morpholino)ethansulfonic acid (MES) and bis-tris propane (BTP). In one embodiment, a buffer mixture comprises citrate and bicine. In one embodiment, a buffer mixture comprises cacodylate and HEPES.

The buffer mixtures as disclosed above are designed to provide a stable analysis platform such that the buffer's themselves, do not affect protein melting point temperatures as a result of altering physical parameters of the buffer mixture.

III. Plate Layout and Control

In one embodiment, the present invention contemplates a kit comprising a well plate having a plurality of wells. In one embodiment, the well plate comprises ninety-six (96) test wells. In one embodiment, the well plate is divided into multiple subsections, wherein each subsection contains a series of test wells that comprise different test components, wherein each test component measures a different parameter across a physiologically relevant range. In one embodiment, each well plate comprises a control well. In one embodiment, the control well comprises a test protein sample and a cognate buffer. In one embodiment, the control well lacks any reagent and/or component from said kit. In one embodiment, the test protein sample is diluted with the cognate buffer at the same ratio as the test wells. Although it is not necessary to understand the mechanism of an invention, it is believed that the control well serves as a baseline for subsequent data interpretation. In one embodiment, the well plate is a higher order well plate comprising a ninety-six well multiple. In one embodiment, the kit provides test well formats to perform broad protein screens. In one embodiment, the broad protein screen comprises a protein stability custom designed buffer formulation screen. In one embodiment, the broad protein screen comprises a protein cryprotectant custom designed buffer formulation screen. In one embodiment, the broad protein screen comprises a protein quality control screen. In one embodiment, the kit provides a total protein profiler screen wherein the protein stability custom designed buffer formulation screen, the protein cryoprotectant custom designed buffer formulation screen and the protein quality control screen are simultaneously performed on a single well plate.

IV. Custom Designed Buffers that Maximize Protein Stability

In one embodiment, the present invention contemplates a method comprising a physiologic buffer mixture having a temperature-stable pKa to identify test compounds that increase stability of a sample protein by performing a protein melting point temperature screen. In one embodiment, the screen measures the effects of test compounds including, but not limited to, pH, buffers, divalent ions, Hofmeister series ion, amino acids, urea, ammonium sulphate and/or dimethyl sulfoxide. Although it is not necessary to understand the mechanism of an invention it is believed that a protein stability screen acts to define the bulk properties of a solution system (i.e. impact of pH, ionic strength, buffer etc.) and not just one specific component like most of the other screening conditions. The buffer system also acts as an internal control that simultaneously compares new and old conditions under identical conditions. Although commonly used previously, a urea stability test provides validation and verification of all testing parameters by comparative analysis with historical literature. DMSO screening allows for the nomination of conditions where protein compounds are usually insoluble (e.g., for example, drug binding studies) to identify the proper use of DMSO to solubilize these compounds without effecting the performance of the intended assay.

In one embodiment, the present invention contemplates a protein stability method that comprises simultaneous comparative screening of various molecules to determine their relative effects under identical conditions (e.g., buffer composition, pH, temperature etc.).

In one embodiment, the present invention contemplates a method for determining protein stability comprising; a) a solid substrate comprising a plurality of wells wherein each of said plurality of wells contains an identical concentration of a physiologic buffer mixture comprising at least two buffers and has a stable pKa over a temperature range of between 0-100° C., an identical concentration of a protein and a different concentration of an identical test compound; b) determining a melting temperature of said protein in each of said plurality of wells to create a protein melting point temperature profile; c) observing an increased protein melting point temperature as compared to a control in said profile that identifies an improved stability effect on said protein by said test compound.

Figure 2:
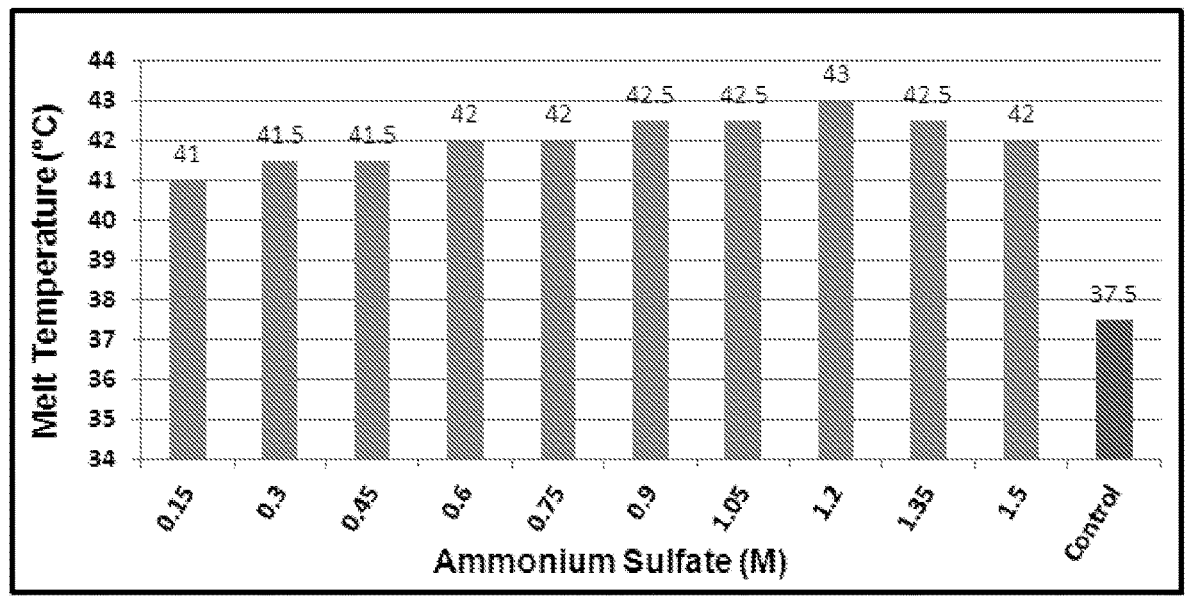
FIG. 2 presents exemplary data showing a protein temperature melting point profile as determined by ammonium sulphate in a MES/BTP buffer mixture.
Figure 3:
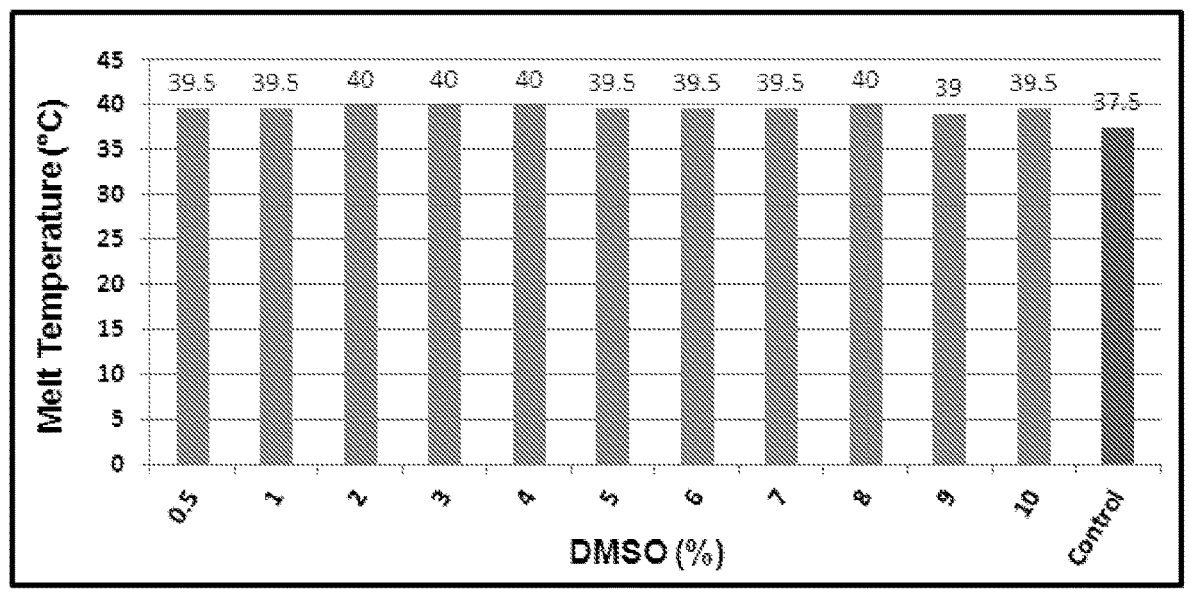
FIG. 3 presents exemplary data showing a protein temperature melting point profile as determined by dimethyl sulfoxide in a MES/BTP buffer mixture.
Figure 4:
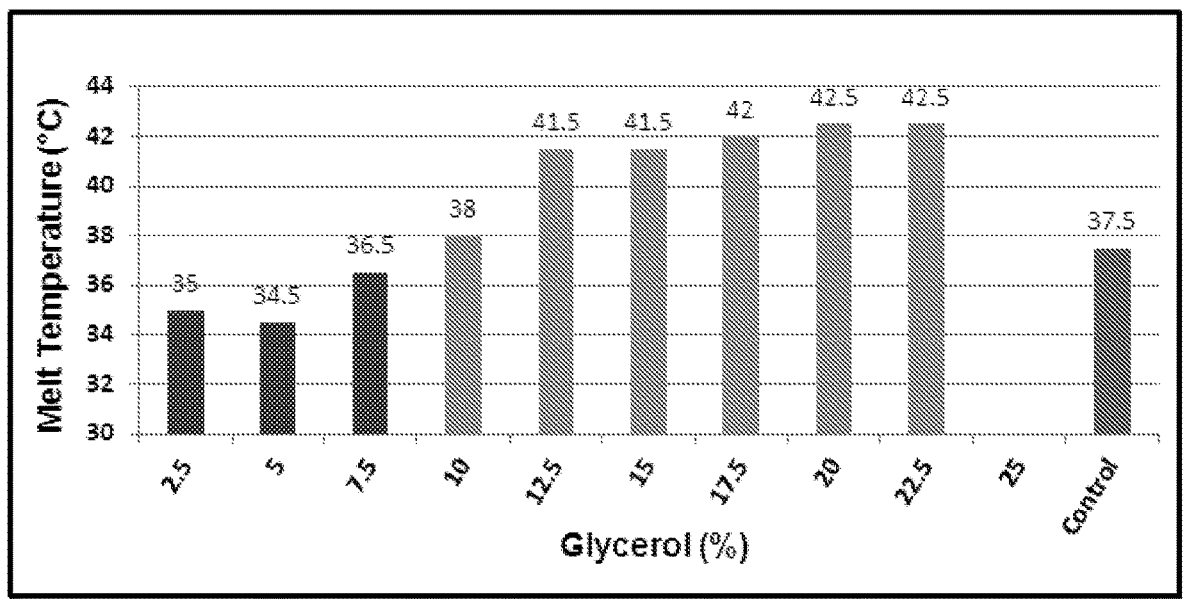
FIG. 4 presents exemplary data showing a protein temperature melting point profile as determined by glycerol in a MES/BTP buffer mixture.
Figure 5:
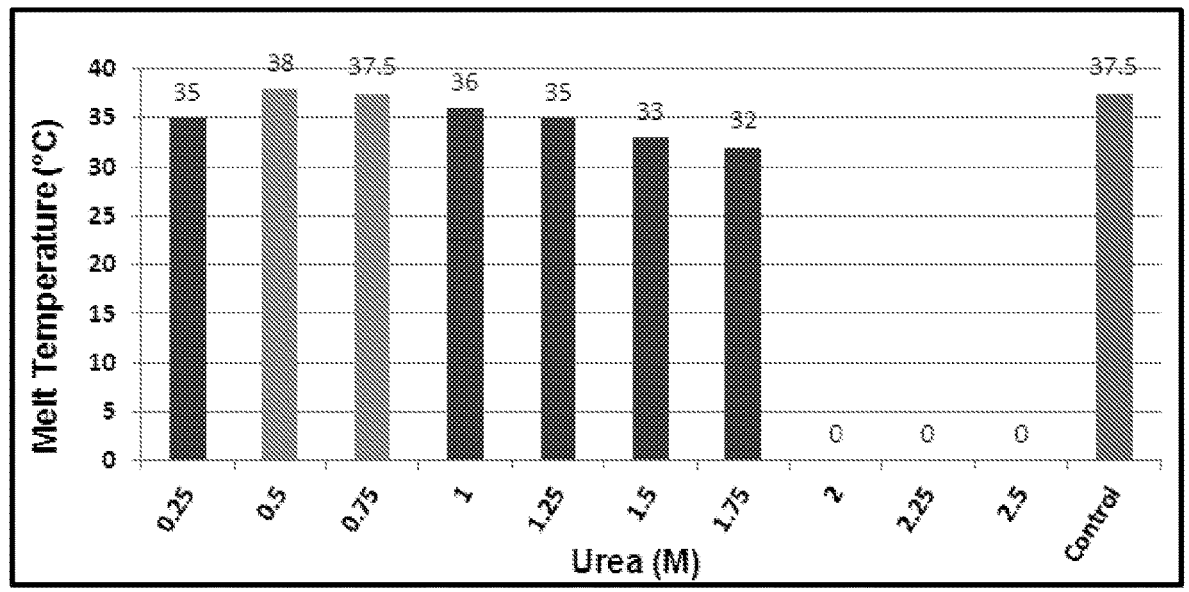
FIG. 5 presents exemplary data showing a protein temperature melting point profile as determined by urea in a MES/BTP buffer mixture.
Figure 6:
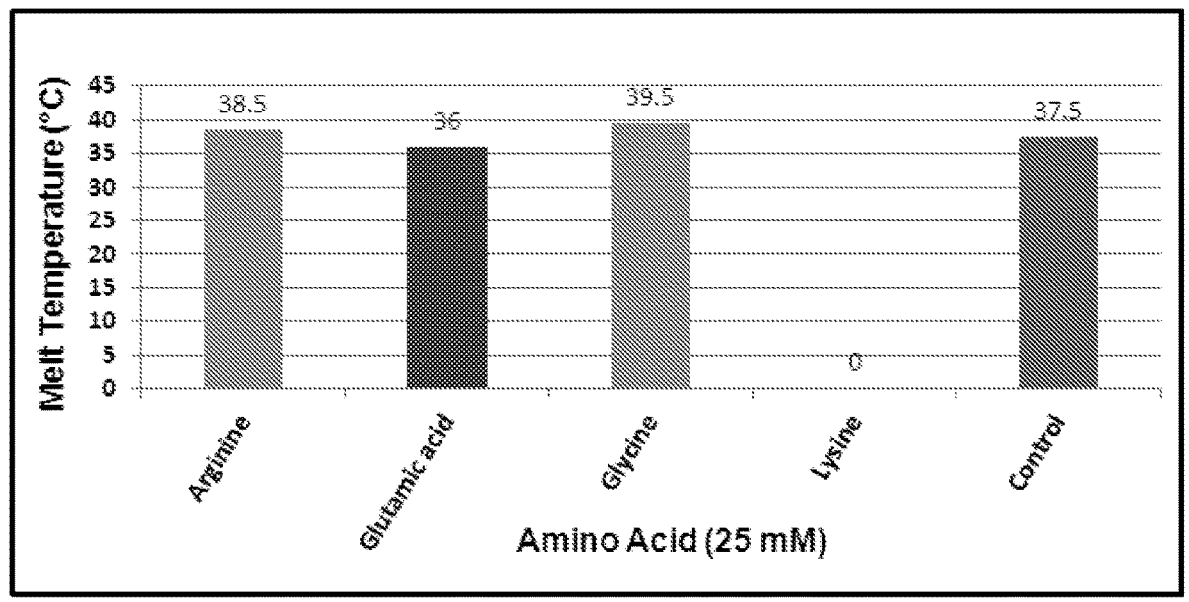
FIG. 6 presents exemplary data showing a protein temperature melting point profile as determined by various amino acids in a MES/BTP buffer mixture.

Hydrogen ion concentration (e.g., pH) was shown to effect protein stability by altering a protein melting temperature points of between 0-40° C. in a buffer mixture comprising MES and BTP over a pH range of between 5-9. See, FIG. 1. In particular, the protein appeared more stable over a pH range of 6.5-7.5 and between 8.5-9 as indicated by the observed increases in protein melting point temperatures. These data suggest that pH 7 may be selected as component for a customized buffer system for this protein. The effects of ammonium sulphate has been tested using a buffer mixture of MES and BTP. See, FIG. 2. As expected, even low concentrations of ammonium sulphate significantly elevated protein melting point temperatures thereby stabilizing the protein. These data suggest that 1.2 M ammonium sulphate may be selected as a component for a customized buffer system for this protein. On the other hand, dimethyl sulfoxide (DMSO) consistently increased protein melting point temperatures when tested using a buffer mixture of MES and BTP as the protein melting point temperature remained constant at all DMSO concentrations. See, FIG. 3. These data suggest that a range of 0.5-10% DMSO may be selected as a component for a customized buffer system for this protein. A single phase effect of glycerol was observed, where glycerol concentrations below 10% lowered the protein melting point temperature thereby destabilizing the protein, while glycerol concentrations above 10% raised the protein melting temperature thereby stabilizing the protein. See, FIG. 4. These data suggest that 20 or 22.5% glycerol may be selected as a component for a customized buffer system for this protein. A generalized decrease in protein stability was seen with urea, where lower protein melting point temperatures were observed (e.g., protein destabilization) at concentrations either under 0.5 M or between 0.75-1.75 M. Urea concentrations in excess of 1.75 M resulted in complete protein denaturation such that no melting point temperature was determinable. See, FIG. 5. These data suggest that urea should not be selected as a component for a customized buffer system for this protein. Data was also collected using various amino acids demonstrating differential effects on protein melting point temperatures. See, FIG. 6. These data suggest that arginine and glycine may be selected as a component for a customized buffer system for this protein, while glutamic acid should not be included.

Figure 7:
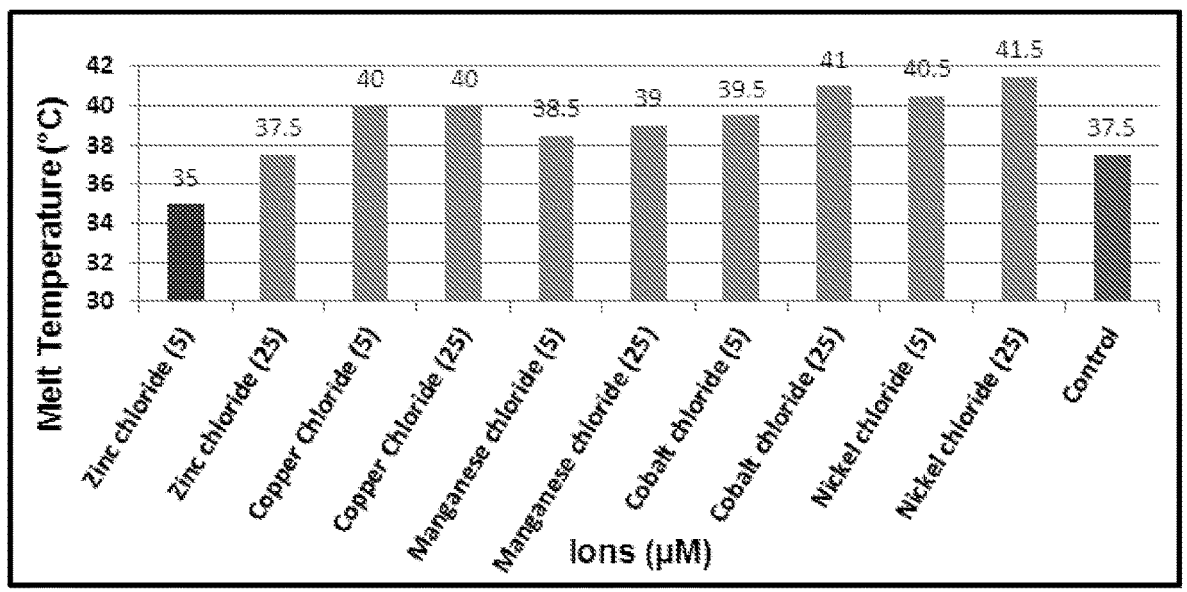
FIG. 7 presents exemplary data showing a protein temperature melting point profile as determined by an inorganic ion screen in a MES/BTP buffer mixture.
Figure 8:
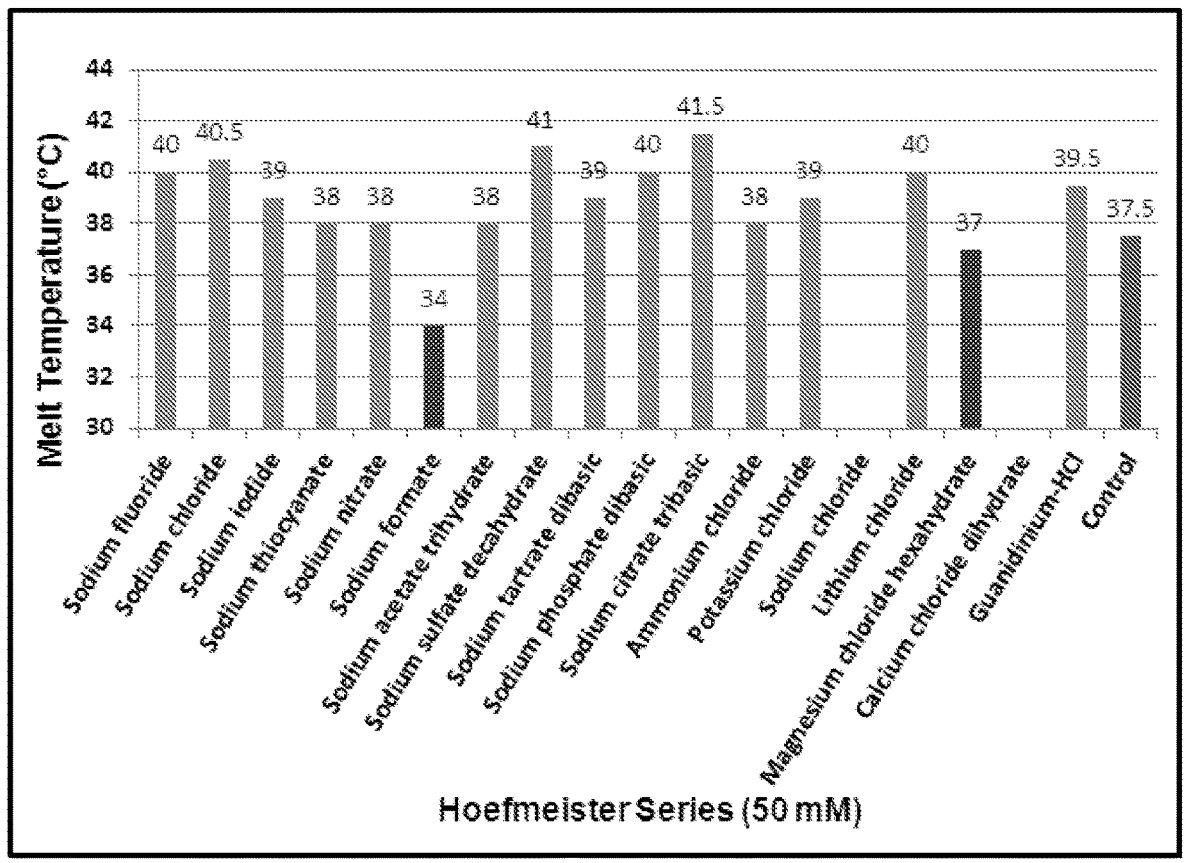
FIG. 8 presents exemplary data showing a protein temperature melting point profile as determined by a Hoefmeister Series inorganic ion screen in a MES/BTP buffer mixture.

A metal ion screen was performed that compared the relative effects of five (5) different metal chloride ions, each at two different concentrations. See, FIG. 7. These metal chloride ions were zinc chloride, copper chloride, manganese chloride, cobalt chloride and nickel chloride each tested at 5 μM and 25 μM. It can be seen that differential effects on protein $T_m$ were observed. These data suggest that the nickel chloride, cobalt chloride, manganese chloride and copper chloride ions may be selected for inclusion in a customized buffer system for this protein, but that zinc chloride should not be included. A standard Hoefmeister Series screen of inorganic ions also show differential effects on protein melting point temperatures. See, FIG. 8. These data suggest that sodium format and magnesium chloride hexahydrate should not be included in a customized buffer system for this protein, sodium fluoride, sodium chloride, sodium iodide, sodium thiocynate, sodium nitrate, sodium acetate trihydrate, sodium sulphate decahydrate, sodium tartrate dibasic, sodium phosphate dibasic, sodium citrate tribasic, ammonium chloride, potassium chloride, lithium chloride, calcium chloride dihydrate and guanidinium hydrochloride may be selected as a component because they all improved the stability of the protein as demonstrated by the higher $T_m$.

Figure 9:
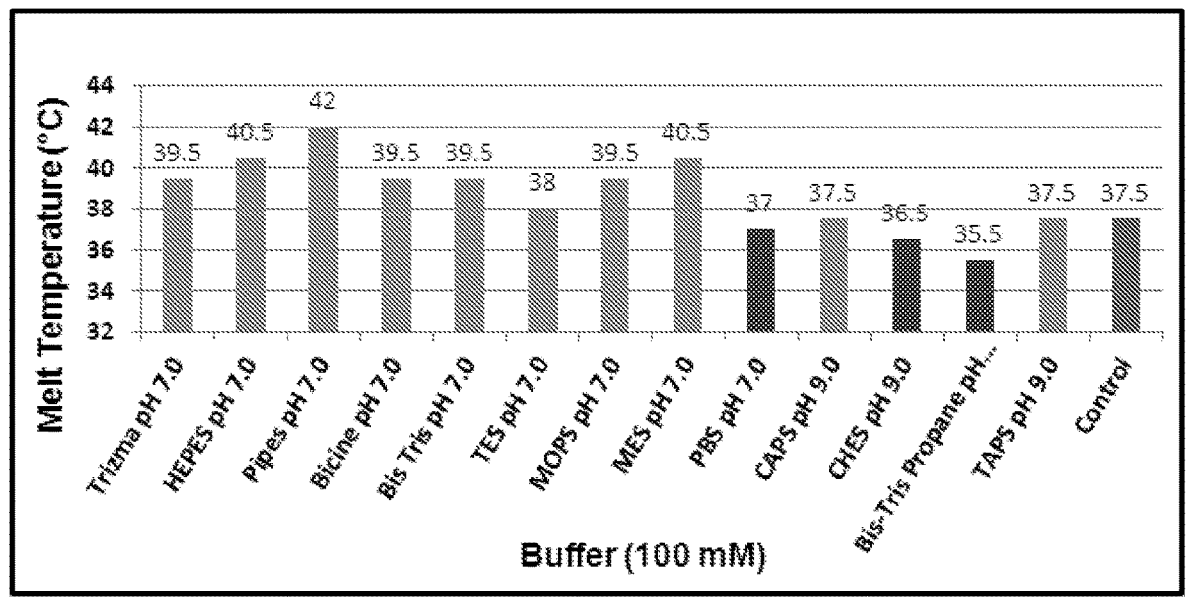
FIG. 9 presents exemplary data showing a protein temperature melting point profile as determined by a physiologic third buffer screen at selected pH levels in a MES/BTP buffer mixture.

Data comparing the effect of the following third buffers at pH 7 included Trizma, HEPES, Pipes, Bicine, Bis Tris, TES, MOPS, MES and PBS or at pH 9 included CHES, Bis-Tris Propane and TAPS. See, FIG. 9. It can be observed that all tested buffers at pH 7, with the exception of phosphate buffered saline, improved protein stability by demonstrating an increase in protein melting point temperature and may be selected as a component for inclusion in a customized buffer system for this protein.

V. Custom Designed Buffers that Maximize Protein Cryoprotection

In some embodiments, the present invention contemplates a method that is used to nominate and/or optimize buffer parameters that increase protein cryoprotection. In some embodiments, the buffer parameters are cryoprotectant test compounds that increase the protein melting point temperature and thereby makes the protein more stable in freezing conditions. Although it is not necessary to understand the mechanism of an invention, it is believed that the identification of buffer parameters that increase protein melting point temperatures provide a physiologic liquid buffer mixture that is conducive to cryoprotection by: i) reducing protein loss to aggregation and/or precipitation over time during frozen storage; and ii) reducing degradation-induced loss in protein activity upon thawing.

In some embodiments, the present invention contemplates a cryoprotection screen comprising a single buffer mixture and cryoprotectant test compounds that, when used in conditions of increasing temperature are: i) aqueous-based; ii) depress the melting point of water; iii) do not precipitate or form eutectics or hydrates; and iv) are relatively non-toxic at efficacious concentrations. In one embodiment, the cryoprotectant test compounds include, but are not limited to, polyols, alcohols, salts, non-volatile organics, osmolytes and/or sugars.

In one embodiment, the present invention contemplates a method for identifying a cryoprotection compound for inclusion in a protein-specific buffer system comprising; a) a solid substrate comprising a plurality of wells wherein each of said plurality of wells contains an identical concentration of a physiologic buffer mixture comprising at least two buffers and has a stable pKa over a temperature range of between 0-100° C., an identical concentration of a protein and a different concentration of an identical cryoprotectant test compound; b) determining a melting temperature of said protein in each of said plurality of wells to create a protein melting point temperature profile; and c) observing an increased protein melting point temperature as compared to a control in said profile that identifies a cryoprotectant effect on said protein by said test compound demonstrated by an increased protein melting point as compared to a control protein melting point.

Figure 10:
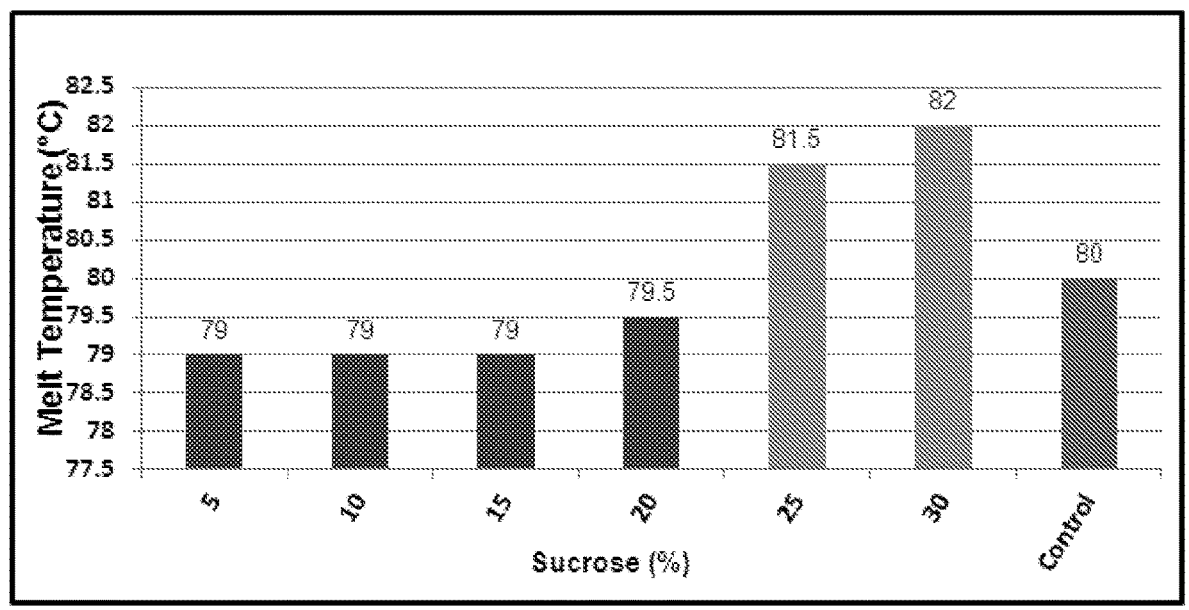
FIG. 10 presents exemplary data showing a protein temperature melting point profile as determined by sucrose in a MES/BTP buffer mixture.
Figure 11:
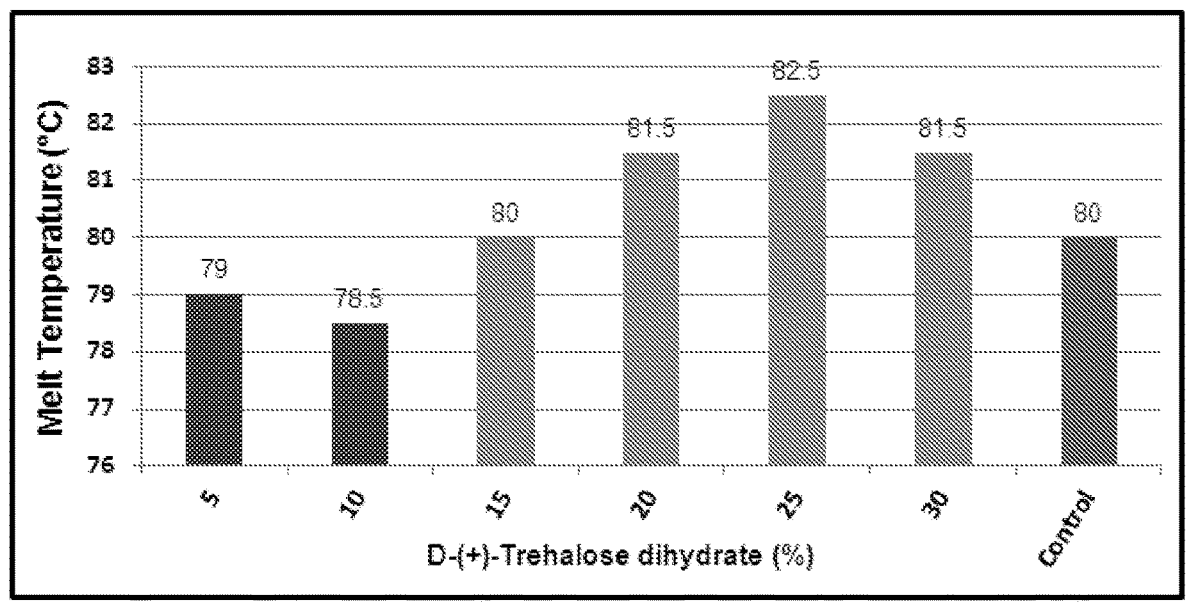
FIG. 11 presents exemplary data showing a protein temperature melting point profile as determined by trehalose in a MES/BTP buffer mixture.
Figure 12:
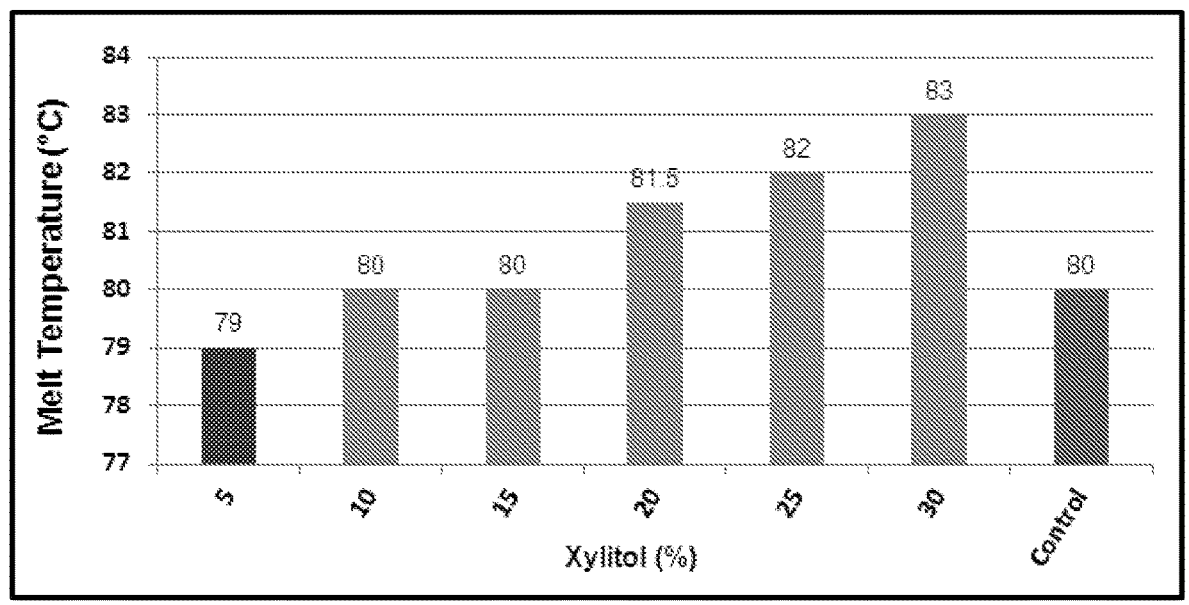
FIG. 12 presents exemplary data showing a protein temperature melting point profile as determined by xylitol in a MES/BTP buffer mixture.

The data presented herein demonstrates a protein melting point temperature point screen that selects compounds for inclusion in a customized cryopreservation buffer system for a specific protein by observing increased protein melting point temperature points as compared to control. For example, a protein melting point temperature screen was performed using sucrose at several different concentrations. It was determined that this compound raised the melting point temperature at a concentration of 25% sucrose and 30% sucrose. See, FIG. 10. These data suggest that 25 or 30% sucrose may be selected for inclusion in a customized buffer system for this protein. The data also show that trehalose may be an even more effective cryoprotectant as the increase in protein melting temperature is more pronounced than sucrose. See, FIG. 11. These data suggest that 25% trehalose may be selected for inclusion in a customized buffer system for this protein. Xylitol also was observed to have significant cryoprotectant effects as it raised the protein melting temperature a full degree in comparison to sucrose or trehalose (e.g., for example, 30%). See, FIG. 12. These data suggest that 30% xylitol may be selected for inclusion in a customized buffer system for this protein.

Figure 13:
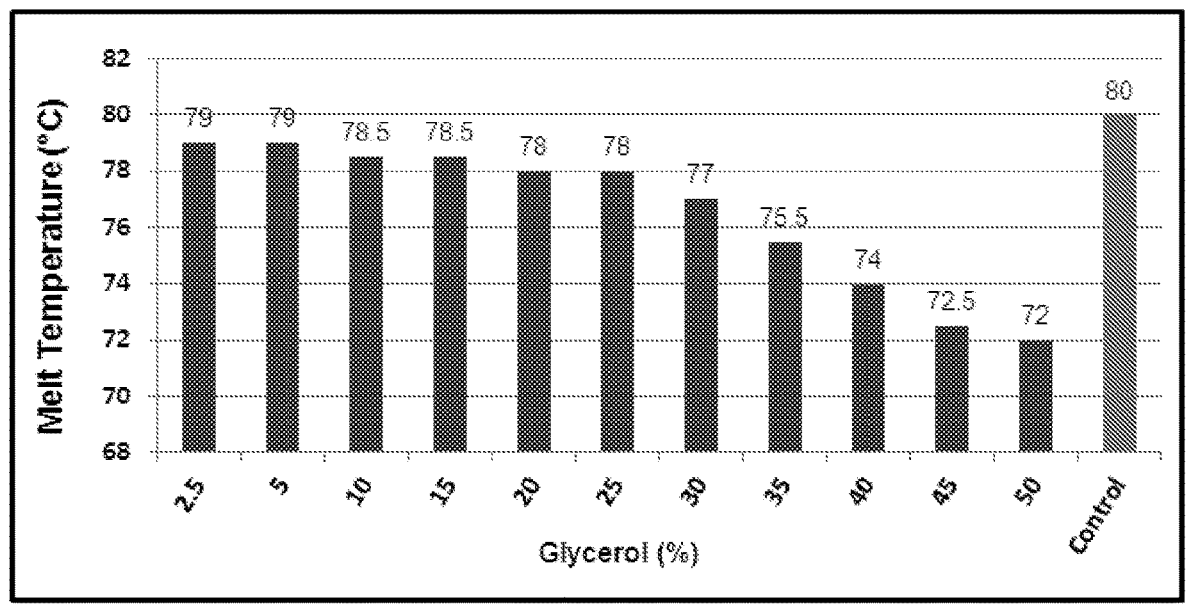
FIG. 13 presents exemplary data showing a protein temperature melting point profile as determined by glycerol in a MES/BTP buffer mixture.
Figure 14:
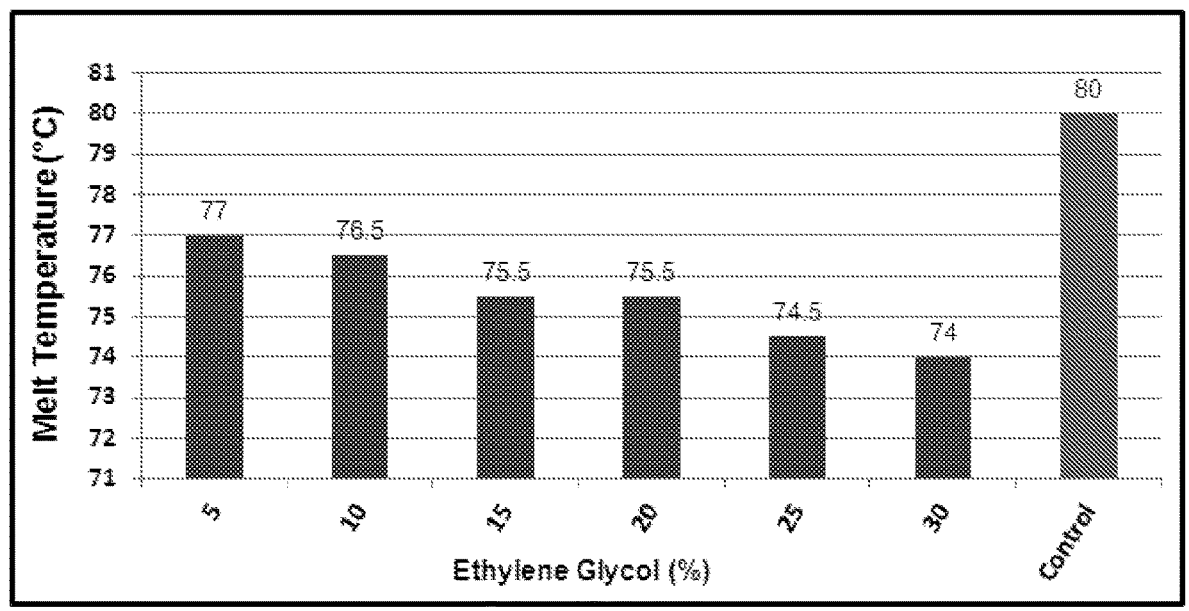
FIG. 14 presents exemplary data showing a protein temperature melting point profile as determined by ethylene glycol in a MES/BTP buffer mixture.

Conversely, the present method can also identify compounds that might not be expected to provide quality cryoprotectant effects. For example, glycerol is widely accepted to provide cryoprotection. However, the data presented here shows that not to be the case as glycerol results in a dose-dependent decrease in protein melting point temperature. See, FIG. 13. These data suggest that glycerol should not be included in a custom buffer system for this protein. This is opposite to what one would expect for an indicative parameter to identify a quality cryoprotectant. These data suggest that degradation of protein within weeks after freezing in 50% glycerol may be prevented by using trehalose as a cryoprotectant. Although it is not necessary to understand the mechanism of an invention, it is believed that the use of such an improved cryoprotectant improves stability for nearly two years. Similar results were seen for ethylene glycol another compound on might expect to have cryoprotectant effects. However, this data also shows a dose-dependent decrease in protein melting point temperatures. See, FIG. 14. These data suggest that ethylene glycol should not be included a custom buffer system for this protein.

VI. Protein Quality Control Assays

In one embodiment, the present invention contemplates a method comprising a protein quality control screen. Although it is not necessary to understand the mechanism of an invention, it is believed that a quality control screen may be used to analyze: i) comparison of protein state prior to storage and post storage; ii) protein synthesis/purification lot-to-lot comparison; and iii) protein synthesis/purification batch testing. In one embodiment, the protein quality control screen measures protein melting point temperature while varying both pH concentration and ionic strength (e.g., for example, using a sodium chloride dose response curve). See, Table 1.

TABLE I

Exemplary Experimental Design For A Protein Quality Control Screen

| pH | NaCl Concentration | | | | | | | | |
|---|---|---|---|---|---|---|---|---|---|
| | 0.125 | 0.25 | 0.5 | 0.75 | 1 | 1.25 | 1.5 | 1.75 | 2 |
| 5 | 73 | 73.5 | 74.5 | 76 | 76.5 | 77 | 77 | 76.5 | 77 |
| 5.5 | 75 | 75 | 75 | 76 | 76.5 | 77 | 77 | 77.5 | 77.5 |
| 6 | 75 | 76 | 76 | 76.5 | 77 | 77 | 77 | 78 | 77.5 |
| 6.5 | 76 | 76.5 | 76.5 | 77 | 77.5 | 77.5 | 77.5 | 78 | 78 |
| 7 | 76 | 76.5 | 77 | 77.5 | 77.5 | 77.5 | 77.5 | 77 | 77 |
| 7.5 | 76.5 | 77.5 | 77.5 | 78 | 77.5 | 76.5 | 76 | 76 | 75 |
| 8 | 75.5 | 77.5 | 76.5 | 77.5 | 76.5 | 76.5 | 76 | 75 | 74.5 |
| 8.5 | 75 | 75.5 | 76 | 77 | 76 | 75 | 75 | 75 | 74.5 |
| 9 | 75 | 75 | 75.5 | 75 | 75 | 75 | 75 | 74.5 | 74 |

Figure 15:
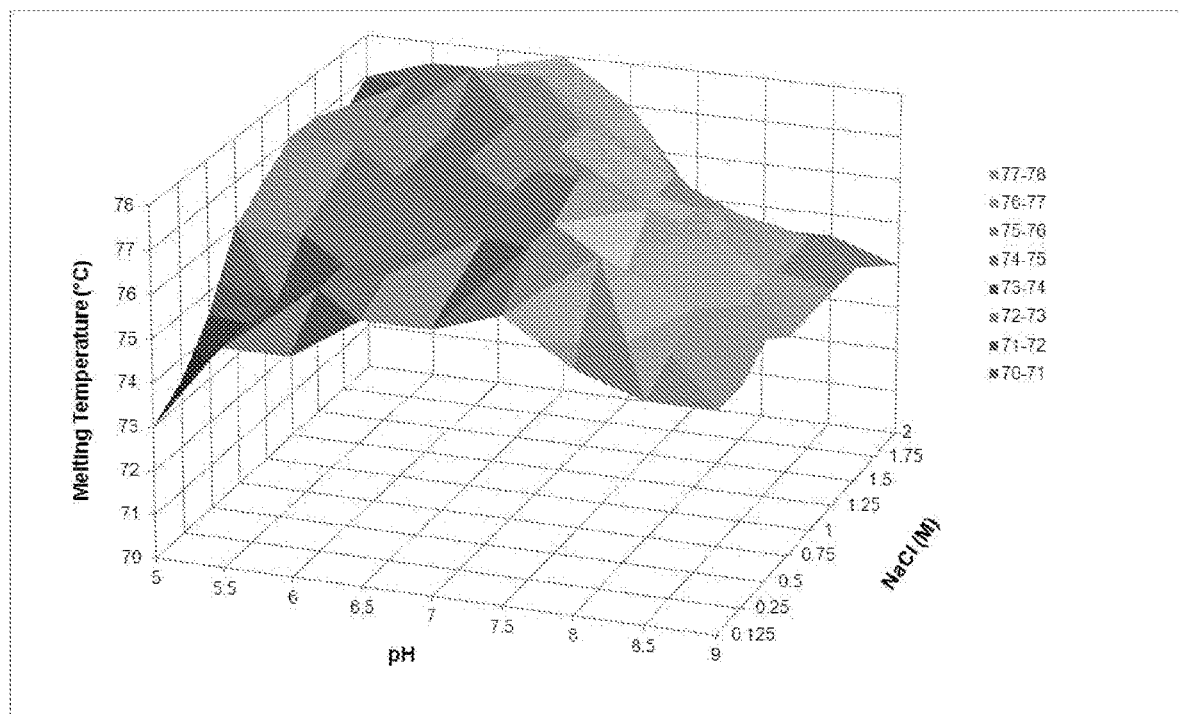
FIG. 15 presents' exemplary data showing a three-dimensional map of protein melting point temperatures plotted against pH concentration and ionic strength (e.g., sodium chloride concentration) generated during a protein quality control screen.

In one embodiment, a three dimensional map of the protein melting point temperatures is created by plotting the melting point determinations relative to pH and ionic strength. See. FIG. 15.

In some embodiments, a protein quality control analysis generates a three-dimensional map at the time of protein production and just prior to protein storage. Subsequently, when the protein is thawed, the exact analysis is repeated to generate a second three-dimensional map. A statistical analysis of the variance between the two maps is used to analyze whether the state of the protein has changed (e.g., indicating, for example, degradation). If the variance falls within a specified tolerance range, the thawed protein may be considered equivalent to the de novo produced protein. Although it is not necessary to understand the mechanism of an invention, it is believed that the method identifies that the material is identical to previous batches and may result in accurate data that is directly comparable to previous experimental results.

VI. Stability Index

Figures 16, 16C:
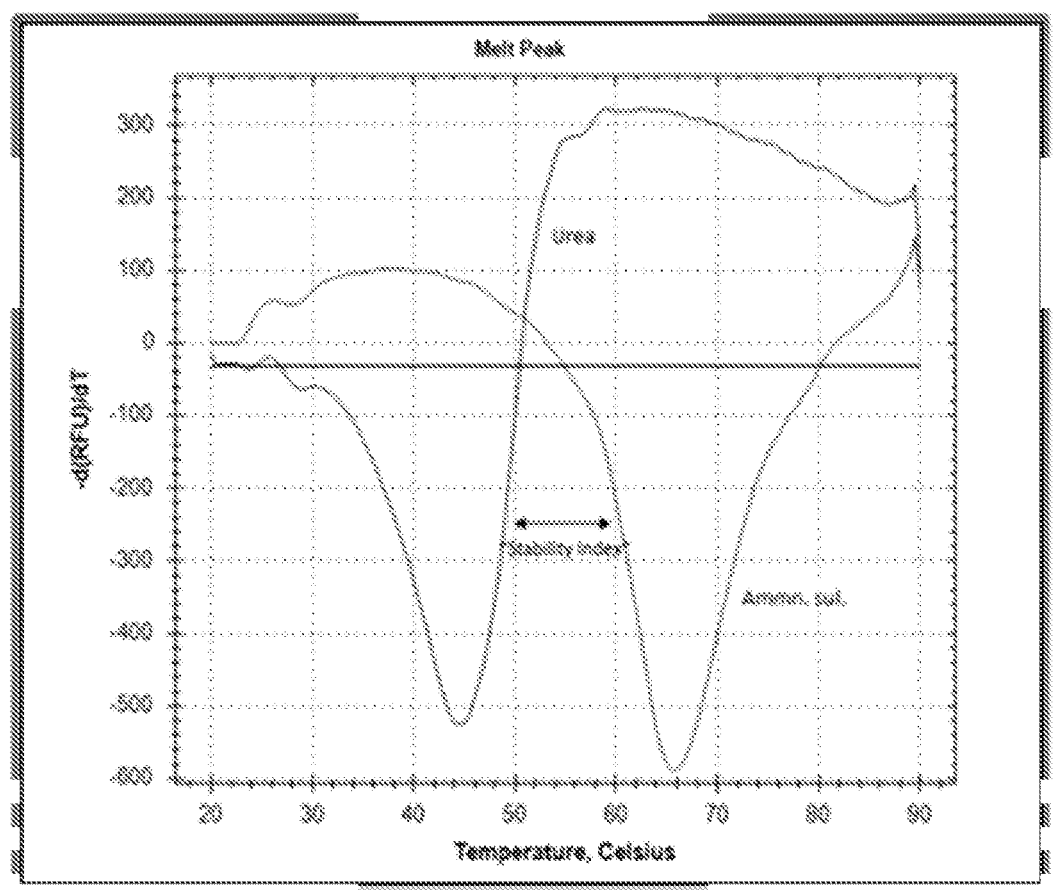
FIG. 16 presents exemplary data showing the construction of a stability index by measuring protein melting point deviations between urea and ammonium sulphate concentration screens. The present data were collected with the Dwarf27 protein (D27).
FIG. 16C: A comparative plot of urea and ammonium sulphate concentration effects on protein stability to identify a protein stability index.

Many methods have been used to describe protein stability. A primary method of early literature was the urea degradation study. As a point of comparative reference to this early literature, the present invention maintains a concentration dependent measure of protein stability relative to urea concentration. Additionally, the present invention provides a concentration dependent analysis of ammonium sulphate. In one embodiment, the presence of urea results in protein destabilization as demonstrated by the generalized decreases in protein $T_m$ as compared to the control $T_m$. See, FIG. 16A. In one embodiment, the presence of ammonium sulphate results in protein stabilization as demonstrated by a concentration-dependent increase in protein $T_m$ as compared to the control $T_m$. See, FIG. 16B.

In one embodiment, the present invention contemplates a method comprising calculating a stability index by dividing an ammonium sulphate-induced change in protein melting point temperature by a urea-induced change in protein melting point temperature. See, FIG. 16C. Although it is not necessary to understand the mechanism of an invention, it is believed that the stability index compares the most stable state possible (e.g., in the presence of an optimal ammonium sulphate concentration) to the most unstable state possible (e.g., in the presence of an optimal urea concentration) at which the denaturing conditions result in protein unfolding. In one embodiment, the difference between the most stable ammonium sulphate point and the least stable urea point (i.e., protein denaturation) describes protein stability and can be compared to results from other subsequent screen (e.g., for example, a screen to optimize buffer conditions).

Although it is not necessary to understand the mechanism of an invention, it is believed that a protein stability index is a mathematical comparison of a melting temperature at an inflection point of an ammonium sulphate concentration curve, divided by a melting temperature at an inflection point of a urea concentration curve. For example, a stable protein would be expected to have a urea melting point temperature and an ammonium sulphate melting point temperature to be identical (e.g., stability index=1). This situation, however, is rarely if ever, observed. In general, therefore, a small deviation between a urea melting point temperature and an ammonium sulphate melting point temperature calculates a low stability index thereby identifying a stable protein. On the other hand, a large deviation between a urea melting point temperature and an ammonium sulphate melting point temperature calculates a high stability index thereby identifying an unstable protein.

VII. Optimization of Chemical Formulations

In one embodiment, the present invention contemplates a protein melting point temperature screen comprising a physiological buffer mixture comprising at least two buffers that maintain an accurate and stable pH measure over 0-100° C. temperature range.

A. pH Stability

One of the largest problems with developing protein melting point temperature screens using a thermal melting platform was process-induced environmental changes resulting from the increasing temperatures. For example, this was of particular importance when trying to accurately measure the pH of a solution across a wide range (e.g., for example pH 5-9) at various temperatures. In one embodiment, the present invention contemplates foundational chemistry used for pH measurements comprising a cohesive buffer component. Although it is not necessary to understand the mechanism of an invention, it is believed that a cohesive buffer component eliminates buffer pKa-induced pH changes, so any pH changes are a result of test protein pKa changes.

Initial trials using common buffers such as phosphate proved inaccurate, non-reproducible and the data was unreliable as demonstrated by $T_m$ variations both above and below a control $T_m$ at various pH levels. See, FIG. 17A. In one embodiment, the present invention contemplates a multi-component single buffer mixture characterized by: i) a low delta specific heat ($C_P$); ii) low buffer-buffer interactions; iii) low divalent cation chelation; and iv) buffering capacity over a wide pH range. In one embodiment, the multi-component single buffer mixture comprises MES and BTP. See, FIG. 17B. This single buffer mixture was shown to reliably increase the protein $T_m$ as compared to a control $T_m$ at all tested pH levels. The optimal pH for Dwarf27 protein was determined by other methods to be pH 7.5 (data not shown).

These data show that the use of a phosphate based buffer system does not provide accurate results. Initial trials using a citrate-only buffer also shows similar inconsistent results as the phosphate based analysis (data not shown). However, a multi-component single buffer mixture comprising citrate and bicine showed similar data as the MES-BTP formulation (data not shown).

B. Reagent Concentration for Effective Measurements

An optimum concentration for each reagent was nominated after the analysis of hundreds of proteins. For example, the pH stability screen was performed at a minimum MES-BTP effective concentration.

VIII. Thermal Cycler/Differential Fluorimeter Instrumentation

A. Thermal Cyclers

The present invention comprises test well plates that are compatible with most, if not all, thermal cycler devices that are configured to provide sufficient heating ranges to perform the protein temperature melting point scans as described herein.

A thermal cycler (also known as a thermocycler, RT-PCR machine or DNA amplifier) is a laboratory apparatus most commonly used to amplify segments of DNA via the polymerase chain reaction (PCR). Weier et al. (1988). "A programmable system to perform the polymerase chain reaction." DNA 7(6):441-447. Thermal cyclers may also be used in laboratories to facilitate other temperature-sensitive reactions, including but not limited to, protein denaturation, restriction enzyme digestion and/or rapid diagnostics. Higgins et al., (2003) "A handheld real time thermal cycler for bacterial pathogen detection" Biosensors and Bioelectronics 18(9):1115-1123. Such devices may have a thermal block with holes where tubes holding the reaction mixtures can be inserted. The cycler then raises and lowers the temperature of the block in discrete, pre-programmed steps. Modern thermal cyclers are equipped with a heated lid that presses against the lids of the reaction tubes. This prevents condensation of water from the reaction mixtures on the insides of the lids. Traditionally, a layer of mineral oil was used for this purpose. Some thermal cyclers are equipped with multiple blocks allowing several different reactions to be carried out simultaneously. Some models also have a gradient function to allow for different temperatures in different parts of the block.

Alternatively, thermocycler are available that are configured with well array plates and an optical reaction module to perform automated differential scanning fluorimetry (infra). This configuration allows for rapid data acquisition during the performance high-throughput real-time protein melting point temperature scans in a multi-well plate format (e.g., a 384 well plate format; Bio-Rad, CFX384 Touch™ Real-Time PCR Detection System). Such systems may comprise an optical system using solid-state technology including, but not limited to, filtered Light Emitting Diodes and/or filtered photodiodes. RT-PCR systems are designed to operate either with, or without, a computer, and also may be configured with alternative automation controllers for higher throughput. The computer control systems allow for either program execution control and/or data file collection and data file storage operations compatible with standard laboratory information management systems (LIMS). RT-PCR instruments are known to operate within acceptable laboratory standards. See, Table 2.

TABLE 2

| Acceptable Instrumentation Operating Parameters | |
|---|---|
| Maximum ramp rate, ° C./sec | 2.5 |
| Average ramp rate, ° C./sec | 2 |
| Heating and cooling method | Peltier |
| Lid, ° C. | Heats up to 105 Temperature |
| Range, ° C. | 0-100 |
| Accuracy, ° C. | ±0.2 of programmed target at 90° C. |
| Uniformity, ° C. | ±0.4 well-to-well within 10 sec of arrival at 90° C. Gradient |
| Operational range, ° C. | 30-100 |
| Programmable span, ° C. | 1-24 |

TABLE 2-continued

Acceptable Instrumentation Operating Parameters

Optical Detection

| | |
|---|---|
| Excitation | 5 filtered LEDs |
| Detection | 5 filtered photodiodes |
| Range of excitation/emission wavelengths, nm | 450-690 |
| Sensitivity | Detects 1 copy of target sequence in human genomic DNA |
| Dynamic range | 10 orders of magnitude |

Scan Time

| | |
|---|---|
| All channels, sec | <20 |

Software

| | |
|---|---|
| Operating systems | Windows 7, Windows 8 |
| Multiplex analysis | Up to 4 targets per well |

This instrument may store data on a resident computer optical readable medium and USB ports for stored memory data and/or real time data transmission from a stand-alone hard drive data storage device for performance of repetitive scans.

B. Differential Scanning Fluorimeter

A differential scanning fluorimeter performs an method that was once referred to as a thermal shift assay. A thermal shift assay quantifies the change in thermal denaturation temperature of a protein under varying conditions. The differing conditions that can be examined are very diverse, e.g. pH, salts, additives, drugs, drug leads, oxidation/reduction, or mutations.

Preliminary techniques used 1,8-ANS as a reporter label with quartz cuvettes. Semisotnov et al., (1991) "Study of the "molten globule" intermediate state in protein folding by a hydrophobic fluorescent probe." Biopolymers 31(1): 119-128. High-throughput versions using a plate readers substituted SYPRO Orange as a reporter label instead of 1,8-ANS. Pantoliano et al., (2001). "High-density miniaturized thermal shift assays as a general strategy for drug discovery." Journal of Biomolecular Screening 6(6): 429-440; and Lo et al., (2004) "Evaluation of fluorescence-based thermal shift assays for hit identification in drug discovery." Analytical Biochemistry 332(1):153-159. SYPRO Orange has an excitation/emission wavelength profile compatible with qPCR machines (e.g., thermocyclers) and was termed Differential Scanning Fluorimetry (DSF). Niesen et al., (2007) "The use of differential scanning fluorimetry to detect ligand interactions that promote protein stability." Nature Protocols 2(9): 2212-2221.

SYPRO Orange binds nonspecifically to hydrophobic surfaces, and water strongly quenches its fluorescence. When a protein unfolds, exposed hydrophobic surfaces bind the dye, resulting in an increase in fluorescence by excluding water. A stability curve and its midpoint value (e.g., melting temperature ($T_m$) also known as the temperature of hydrophobic exposure ($T_h$)) are obtained by gradually increasing the temperature to unfold the protein and measuring the fluorescence at each point. Curves are measured for protein only and protein+ligand, and a $\Delta T_m$ is calculated. A DSF assay allows for high-throughput screening of ligands to the target protein and it is widely used in the early stages of drug discovery in the pharmaceutical industry, structural genomics efforts, and high-throughput protein engineering. Ciulli et al., (2007) "Fragment-based approaches to enzyme inhibition." Current Opinion In Biotechnology 18(6):489-496.

IX. Kits

In one embodiment, the present invention contemplates a kit comprising a well plate comprising a lid, wherein each well contains 25 μl of a buffer mixture and a test compound. In one embodiment, the kit also comprises a protein dye. In one embodiment, the kit further comprises a set of instructions for performing a protein temperature melting point screen.

In one embodiment, the kit instructions comprise the following steps:
i) pre-chill the RT-PCR plate at 4° C. for 15-30 minutes prior to the addition of reagents and/or protein sample to each of the wells.
ii) The dye vial and kit plates should be stored at −20° C. and away from light until the time of use.
iii) Add 5 μl of dye to 500 μl of protein sample. The dye to protein ratio can be modified to any particular protein. For example, smaller proteins or proteins with a small hydrophobic core may require an increased dye concentration.
iv) Transfer 5 μl of each solution from the well plate to a corresponding well of the RT-PCR plate.
v) Add 5 μl of the protein/dye mixture to each well of the RT-PCR plate (>0.5 mg/ml).
vi) Mix the solutions by pipetting up and down (~5 times).
   a) gently placing all solutions at the bottom of the avoids subsequent plate centrifugation.
vii) Seal the RT-PCR plate.
viii) Immediately load the TR-PCR plate into the instrument and begin the programmed heating schedule (approximate timeframe=62 minutes), for example:
   a) Heat to 20 C
   b) Ramp to 90 C in 0.5 C increments.
   c) Ramp to 4 C with a two minute schedule.
ix) Upload stored data file to a designated website (e.g., for example, caymanchem.com/deltatm) and follow the instructions. Once the data is entered, the conditions with the largest change in $T_m$ will be displayed and available for electronic delivery.

EXPERIMENTAL

Example I

Dwarf27 Protein Stability Screen

Figures 18, 18A, 18B, 18C, 18D, 18E:
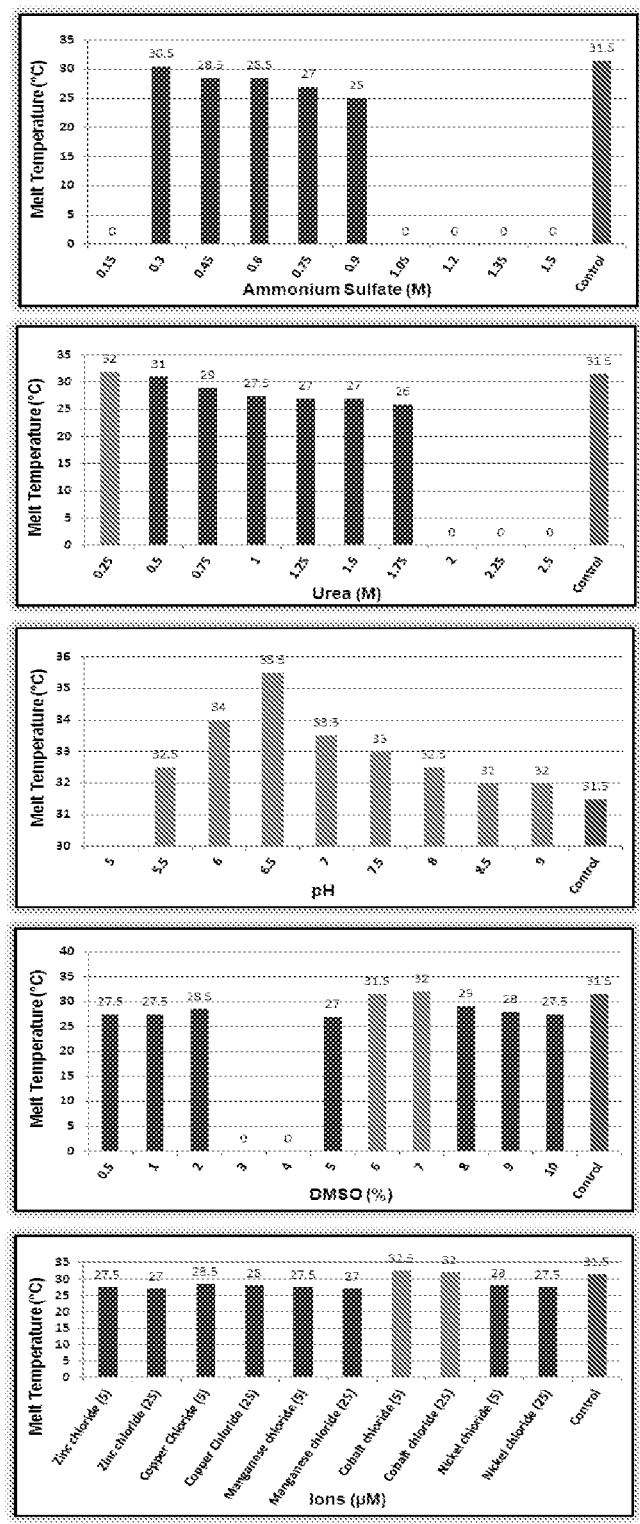
FIG. 18 presents exemplary data showing screening of Dwarf27 protein in an MES-BTP buffer mixture to provide an optimal buffer formulation.
FIG. 18A: An ammonium sulphate screen.
FIG. 18B: A urea screen.
FIG. 18C: A pH screen.
FIG. 18D: A DMSO screen.
FIG. 18E: A metal ion screen.
Figures 18, 18F, 18G, 18H, 18I:
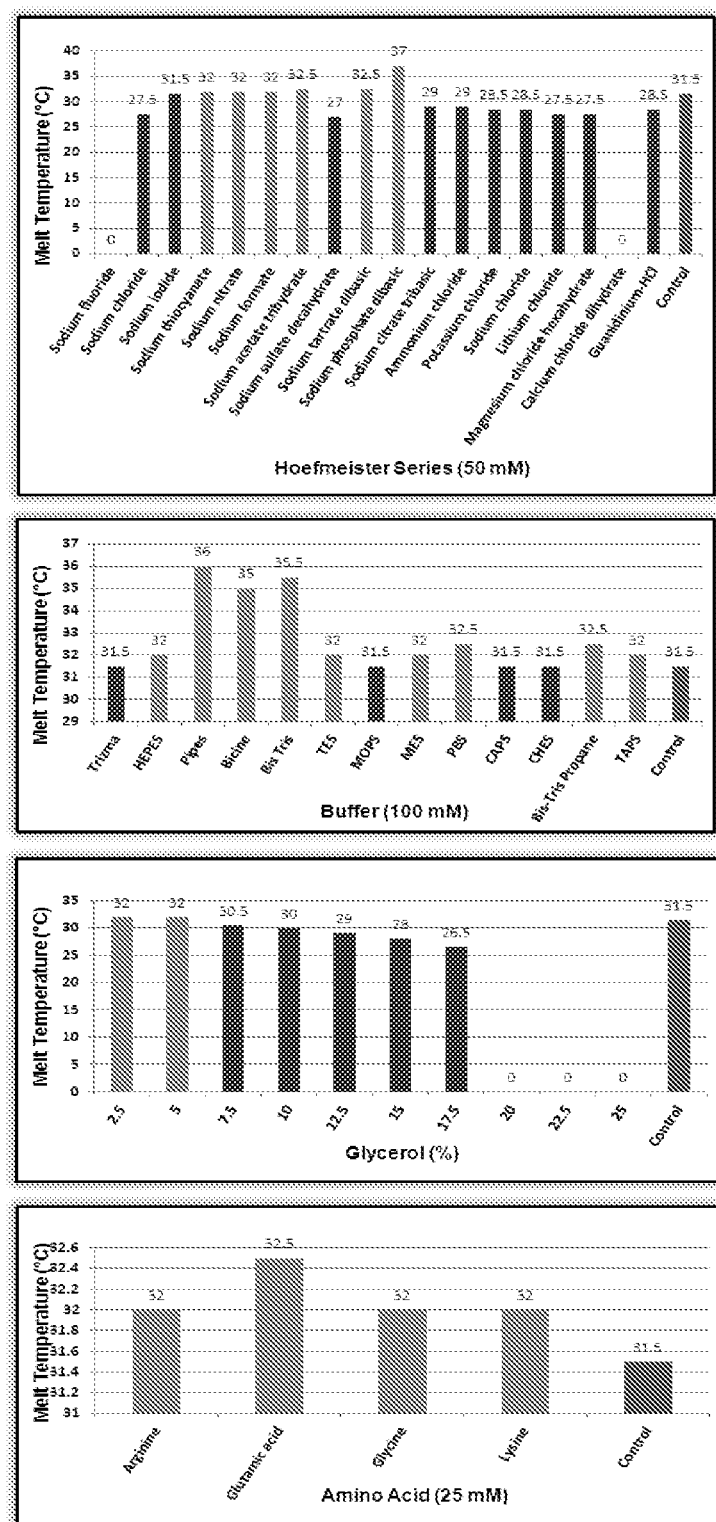
FIG. 18F: A Hoefmiester series screen.
FIG. 18G: A third buffer screen.
FIG. 18H: A glycerol screen
FIG. 18I: An amino acid screen.

The Dwarf27 protein was screened in an MES-BTP buffer mixture to provide an optimal buffer formulation using an integrated analysis of protein melting temperature point data collected from: i) an ammonium sulphate screen (FIG. 18A); ii) a urea screen (FIG. 18B); iii) a pH screen (FIG. 18C); iv) a DMSO screen (FIG. 18D); v) a metal ion screen (FIG. 18E); vi) a Hoefmiester series screen (FIG. 18F); vii) a third buffer screen (FIG. 18G); viii) a glycerol screen (FIG. 18H); and xi) an amino acid screen (FIG. 18I). Data was collected using a Spyro Orange fluorophore.

These data suggest that a customized buffer system for Dwarf27 may include: pH 6.5; 7% DMSO; 5-25 μM cobalt chloride; 50 mM sodium phosphate dibasic; 100 mM PIPES; 2.5% glycerol; and 25 mM glutamic acid.

Figure 19:
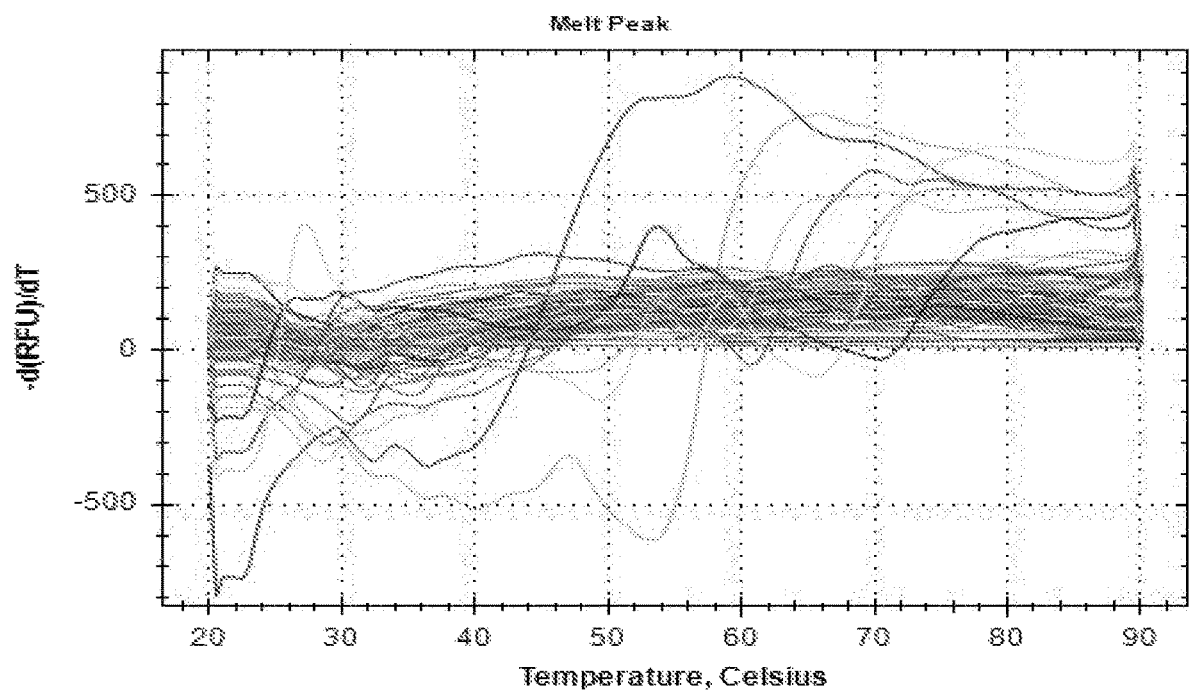
FIG. 19 present exemplary data of an integrated analysis of the D27 protein melting point temperature profiles based upon the data shown in FIGS. 18A-18I. This plot compares the differences in inflection points of these protein melting temperature point profiles to identify buffer components that optimize Dwarf27 protein stability.

The integrated analysis compared the differences in inflection points of these protein melting temperature point screens to identify Dwarf27 protein melting point profiles. See, FIG. 19.

Example II

MX-4 Protein Stability Screen

Figures 20, 20A, 20B, 20C, 20D, 20E:
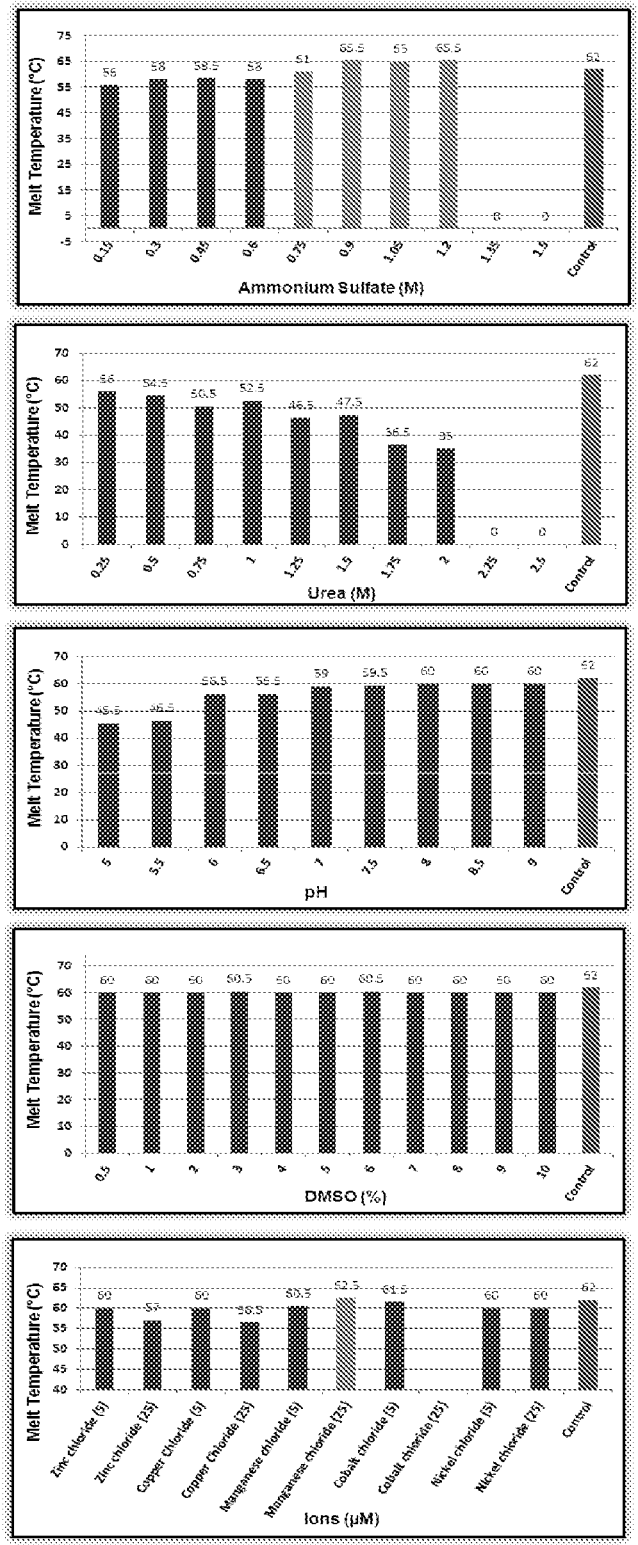
FIG. 20 presents exemplary data showing screening of MX4 protein in an MES-BTP buffer mixture to provide an optimal buffer formulation.
FIG. 20A: An ammonium sulphate screen.
FIG. 20B: A urea screen.
FIG. 20C: A pH screen.
FIG. 20D: A DMSO screen.
FIG. 20E: A metal ion screen.
Figures 20, 20F, 20G, 20H, 20I:
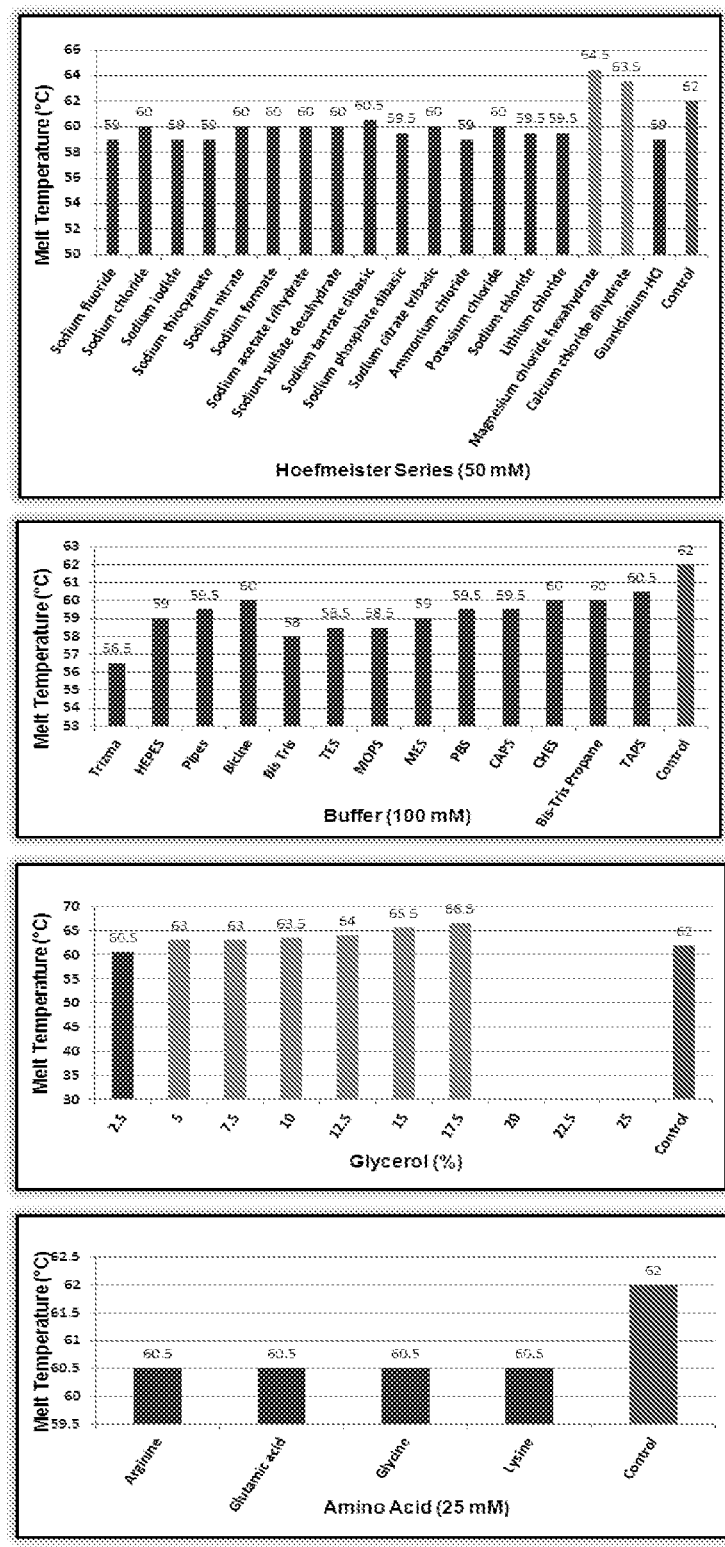
FIG. 20F: A Hoefmiester series screen.
FIG. 20G: A third buffer screen.
FIG. 20H: A glycerol screen
FIG. 20I: An amino acid screen.

The MX-4 protein was screened in an MES-BTP buffer mixture to provide an optimal buffer formulation using an integrated analysis of protein melting temperature point data collected from: i) an ammonium sulphate screen (FIG. 20A); ii) a urea screen (FIG. 20B); iii) a pH screen (FIG. 20C); iv) a DMSO screen (FIG. 20D); v) a metal ion screen (FIG. 20E); vi) a Hoefmiester series screen (FIG. 20F); vii) a third buffer screen (FIG. 20G); viii) a glycerol screen (FIG. 20H); and xi) an amino acid screen (FIG. 20I). Data was collected using a Spyro Orange fluorophore These data suggest that a customized buffer system for MX-4 may include: 1.2 M ammonium sulphate; >9 pH; 25 µM manganese chloride; 50 mM magnesium chloride hexahydrate; 50 mM calcium chloride dihydrate; and 17.5% glycerol.

Figure 21:
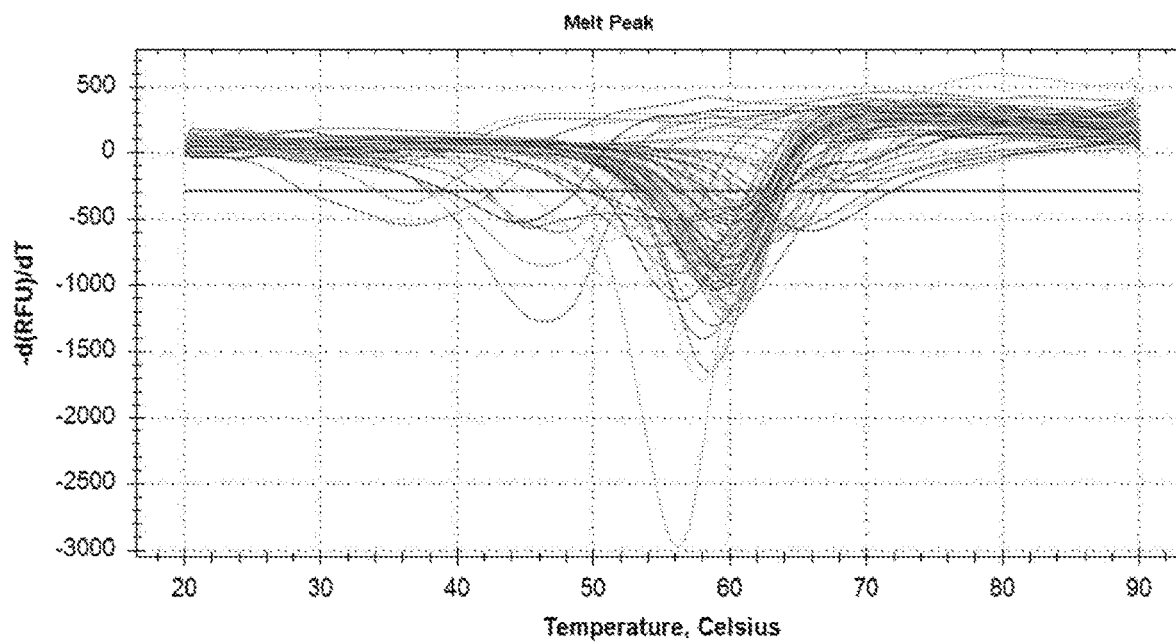
FIG. 21 present exemplary data of an integrated analysis of the MX-4 protein melting point temperature profiles based upon the data shown in FIGS. 20A-20I. This plot compares the differences in inflection points of these protein melting temperature point profiles to identify buffer components that optimize MX-4 protein stability.

The integrated analysis compared the differences in inflection points of these protein melting temperature point screens to identify a MX-4 protein melting point profiles. See, FIG. 21.

Example III

Differential Scanning Fluorimetry

Materials: A fluorometer equipped with temperature control or similar instrumentation (RT-PCR machines); suitable fluorescent dye (e.g., CYPRO Orange); a suitable assay plate, such as 96 well RT-PCR plate.

Compound solutions: Test ligands are prepared at a 50- to 100-fold concentrated solution, generally in the 10-100 mM range. For titration, a typical experimental protocol employs a set of 12 well, comprising 11 different concentrations of a test compound with a single negative control well.

Protein solution: Typically, target protein is diluted from a concentrated stock to a working concentration of ~0.5-5 µM protein with dye into a suitable assay buffer. The exact concentrations of protein and dye are defined by experimental assay development studies.

Centrifugation and oil dispense: A brief centrifugation (~1000×g-force, 1 min) of the assay plate to mix compounds into the protein solution, 1-2 µl silicone oil to prevent the evaporation during heating is overlaid onto the solution (some systems use plastic seals instead), followed by an additional centrifugation step (~1000×g-force, 1 min).

Instrumental set up: A typical temperature ramp rates range from 0.1-10° C./min but generally in the range of 1° C./min. The fluorescence in each well is measured at regular intervals, 0.2-1° C./image, over a temperature range spanning the typical protein unfolding temperatures of 25-95° C. Kranz et al., (2011) "Protein thermal shifts to identify low molecular weight fragments." Methods In Enzymology 493: 277-298.

We claim:

1. A device, comprising:
   a) a solid substrate comprising a plurality of testing wells and a control well, wherein each of said plurality of testing wells comprises a first buffer and a second buffer, said control well comprises a sample buffer, and each of said plurality of testing wells and control well comprises a protein sample;
   b) a first testing well series of said plurality of testing wells, wherein each well of said first testing well series comprises a different ammonium sulphate concentration;
   c) a second testing well series of said plurality of testing wells, wherein each well of said second testing well series comprises a different amino acid;
   d) a third testing well series of said plurality of testing wells, wherein each well of said third testing well series comprises a different urea concentration;
   e) a fourth testing well series of said plurality of testing wells, wherein each well of said fourth testing well series comprises a different glycerol concentration;
   f) a fifth testing well series of said plurality of testing wells, wherein each well of said fifth testing well series comprises a different hydrogen ion concentration;
   g) a sixth testing well series of said plurality of testing wells, wherein each well of said sixth testing well series comprises a different third buffer;
   h) a seventh testing well series of said plurality of testing wells, wherein each well of said seventh testing well series comprises a different dimethyl sulfoxide concentration;
   i) an eighth testing well series of said plurality of testing wells, wherein each well of said eighth testing well series comprises a different Hoefmeister Series compound; and
   j) a ninth testing well series of said plurality of testing wells, wherein each well of said ninth testing well series comprises an different metal ion.

2. The device of claim 1, wherein said device is configured for compatibility with a thermocycler.

3. The device of claim 1, wherein said device is configured for compatibility with an optical reaction module configured with an optically readable storage medium device.

4. The device of claim 1, wherein a first buffer is selected from the group consisting of MES, citrate and cacodylate.

5. The device of claim 1, wherein said second buffer is selected from the group consisting of bis-tris propane, bicine and HEPES.

6. A device, comprising:
   a) a solid substrate comprising a plurality of testing wells and a control well, wherein each of said plurality of testing wells comprises a first buffer and a second buffer, said control well comprises a sample buffer, and each of said testing wells and control well comprises a protein sample;
   b) a first testing well series of said plurality of testing wells, wherein each well of said first testing well series comprises a different ethylene glycol concentration;
   c) a second testing well series of said plurality of testing wells, wherein each well of said second testing well series comprises a different polyethylene glycol 3350 MME concentration;
   d) a third testing well series of said plurality of testing wells, wherein each well of said third testing well series comprises a different erythritol concentration;
   e) a fourth testing well series of said plurality of testing wells, wherein each well of said fourth testing well series comprises a different 2-methyl-2,4 pentanediol concentration;
   f) a fifth testing well series of said plurality of testing wells, wherein each well of said fifth testing well series comprises a different polyethylene glycol 6000 concentration;
   g) a sixth testing well series of said plurality of testing wells, wherein each well of said sixth testing well series comprises a different sodium malonate concentration;
   h) a seventh testing well series of said plurality of testing wells, wherein each well of said seventh testing well series comprises a different ethanol concentration;

i) an eighth testing well series of said plurality of testing wells, wherein each well of said eighth testing well series comprises a different polyethylene glycol 10,000 concentration;
j) a ninth testing well series of said plurality of testing wells, wherein each well of said ninth testing well series comprises an different glycerol concentration;
k) a tenth testing well series of said plurality of testing wells, wherein each well of said tenth testing well series comprises a different xylitol concentration;
l) an eleventh testing well series of said plurality of testing wells, wherein each well of said eleventh testing well series comprises a different sucrose concentration;
m) a twelfth testing well series of said plurality of testing wells, wherein each well of said twelfth testing well series comprises a different trehalose dihydrate concentration;
n) a thirteenth testing well series of said plurality of testing wells, wherein each well of said thirteenth testing well series comprises a different 1,6 hexanediol concentration; and
n) a fourteenth testing well series of said plurality of testing wells, wherein each well of said fourteenth testing well series comprises a different 1,2 propanediol concentration.

7. The device of claim 6, wherein said device is configured for compatibility with a thermocycler.

8. The device of claim 6, wherein said device is configured for compatibility with an optical reaction module configured with an optically readable storage medium device.

9. The device of claim 6, wherein said first buffer is selected from the group consisting of MES, citrate and cacodylate.

10. The device of claim 6, wherein said second buffer is selected from the group consisting of bis-tris propane, bicine and HEPES.

11. A device, comprising:
a) a solid substrate comprising a plurality of testing wells and a control well, wherein each of said plurality of testing wells comprises a first buffer and a second buffer, said control well comprises a sample buffer, and each of said testing wells and control well comprises a protein sample;
b) a first testing well series of said plurality of testing wells comprising a first hydrogen ion concentration, wherein each well of said first testing well series comprises a different sodium chloride concentration;
c) a second testing well series of said plurality of testing wells comprising a second hydrogen ion concentration, wherein each well of said second testing well series comprises a different sodium chloride concentration;
d) a third testing well series of said plurality of testing wells comprising a third hydrogen ion concentration, wherein each well of said third testing well series comprises a different sodium chloride concentration;
e) a fourth testing well series of said plurality of testing wells comprising a fourth hydrogen ion concentration, wherein each well of said fourth testing well series comprises a different sodium chloride concentration;
f) a fifth testing well series of said plurality of testing wells comprising a fifth hydrogen ion concentration, wherein each well of said fifth testing well series comprises a different sodium chloride concentration;
g) a sixth testing well series of said plurality of testing wells comprising a sixth hydrogen ion concentration, wherein each well of said sixth testing well series comprises a different sodium chloride concentration;
h) a seventh testing well series of said plurality of testing wells comprising a seventh hydrogen ion concentration, wherein each well of said seventh testing well series comprises a different sodium chloride concentration;
i) an eighth testing well series of said plurality of testing wells comprising an eighth hydrogen ion concentration, wherein each well of said eighth testing well series comprises a different sodium chloride concentration; and
j) a ninth testing well series of said plurality of testing wells comprising a ninth hydrogen ion concentration, wherein each well of said ninth testing well series comprises a different sodium chloride concentration.

12. The device of claim 11, wherein said device is configured for compatibility with a thermocycler.

13. The device of claim 11, wherein said device is configured for compatibility with an optical reaction module configured with an optically readable storage medium device.

14. The device of claim 11, wherein said first buffer is selected from the group consisting of MES, citrate and cacodylate.

15. The device of claim 11, wherein said second buffer is selected from the group consisting of bis-tris propane, bicine and HEPES.

* * * * *